(12) United States Patent
Thompson et al.

(10) Patent No.: US 7,604,993 B2
(45) Date of Patent: *Oct. 20, 2009

(54) COMBINED REGULATION OF NEURAL CELL PRODUCTION

(75) Inventors: Bradley G. Thompson, Calgary (CA); Samuel Weiss, Calgary (CA); Tetsuro Shingo, Okayama (JP)

(73) Assignee: Stem Cell Therapeutics Inc., Calgary, AB ( * ) Notice: Subject to any disclaimer, the term of this patent is extended or adjusted under 35 U.S.C. 154(b) by 231 days.

This patent is subject to a terminal disclaimer.

(21) Appl. No.: 11/343,419

(22) Filed: Jan. 30, 2006

(65) Prior Publication Data

US 2006/0121007 A1    Jun. 8, 2006

Related U.S. Application Data

(63) Continuation of application No. 10/231,493, filed on Aug. 30, 2002, now Pat. No. 7,048,934.

(60) Provisional application No. 60/316,365, filed on Aug. 30, 2001, provisional application No. 60/316,579, filed on Aug. 31, 2001, provisional application No. 60/322,514, filed on Sep. 14, 2001, provisional application No. 60/386,404, filed on Jun. 7, 2002.

(51) Int. Cl.
*A61K 38/00* (2006.01)
*A61K 38/16* (2006.01)
*A61K 38/18* (2006.01)

(52) U.S. Cl. ............ 435/377; 435/365; 435/368; 424/198.1; 514/12; 530/399

(58) Field of Classification Search ............ None
See application file for complete search history.

(56) References Cited

U.S. PATENT DOCUMENTS

| | | | |
|---|---|---|---|
| 4,703,008 A | 10/1987 | Lin | |
| 4,767,628 A | 8/1988 | Hutchinson | |
| 4,801,575 A | 1/1989 | Pardridge | |
| 4,902,680 A | 2/1990 | Aroonsakul | |
| 5,023,252 A | 6/1991 | Hseih | |
| 5,128,242 A | 7/1992 | Arimura et al. | |
| 5,198,542 A | 3/1993 | Onda et al. | |
| 5,208,320 A | 5/1993 | Kitada et al. | |
| 5,231,178 A | 7/1993 | Holtz et al. | |
| 5,268,164 A | 12/1993 | Kozarich et al. | |
| 5,326,860 A | 7/1994 | Onda et al. | |
| 5,328,860 A | 7/1994 | Lee et al. | |
| 5,441,868 A | 8/1995 | Lin | |
| 5,473,054 A | 12/1995 | Jameson et al. | |
| 5,505,206 A | 4/1996 | Walloch | |
| 5,506,107 A | 4/1996 | Cunningham et al. | |
| 5,506,206 A | 4/1996 | Kozarich et al. | |
| 5,521,069 A | 5/1996 | Onda et al. | |
| 5,527,527 A | 6/1996 | Friden | |
| 5,547,935 A | 8/1996 | Mullenbach et al. | |
| 5,547,993 A | 8/1996 | Miki | |
| 5,559,143 A | 9/1996 | McDonald et al. | |
| 5,614,184 A | 3/1997 | Sytkowski et al. | |
| 5,621,080 A | 4/1997 | Lin | |
| 5,623,050 A | 4/1997 | Kitada et al. | |
| 5,686,416 A | 11/1997 | Kozarich et al. | |
| 5,723,115 A | 3/1998 | Serrero | |
| 5,750,376 A | 5/1998 | Weiss et al. | |
| 5,753,506 A | 5/1998 | Johe | |
| 5,773,569 A | 6/1998 | Wrighton et al. | |
| 5,795,790 A * | 8/1998 | Schinstine et al. | 435/382 |
| 5,801,147 A | 9/1998 | Kitada et al. | |
| 5,833,988 A | 11/1998 | Friden | |
| 5,837,460 A | 11/1998 | Von Feldt et al. | |
| 5,851,832 A | 12/1998 | Weiss et al. | |
| 5,877,169 A | 3/1999 | Simpkins | |
| 5,885,574 A | 3/1999 | Elliott | |
| 5,955,346 A | 9/1999 | Wells et al. | |
| 5,977,307 A | 11/1999 | Friden et al. | |
| 5,980,885 A | 11/1999 | Weiss et al. | |
| 6,015,555 A | 1/2000 | Friden | |
| 6,017,533 A | 1/2000 | Moro et al. | |
| 6,048,971 A | 4/2000 | Sytkowski et al. | |
| 6,165,783 A | 12/2000 | Weiss et al. | |
| 6,191,106 B1 | 2/2001 | Mullenbach et al. | |

(Continued)

FOREIGN PATENT DOCUMENTS

CA    2175992    5/1995

(Continued)

OTHER PUBLICATIONS

Brannvall et al., Molecular and Cellular Neuroscience, vol. 21, Issue 3, Nov. 2002, pp. 512-520.*

(Continued)

*Primary Examiner*—Daniel C Gamett
(74) *Attorney, Agent, or Firm*—Fish & Richardson P.C.

(57) ABSTRACT

This invention relates to a method of selectively producing neural cells, including neurons or glial cells, in vitro or in vivo. Also provided are methods of treating or ameliorating neurodegenerative disease or medical conditions by producing neural cells. Thus, a combination of factors is used to achieve two steps: increasing the number of neural stem cells and instructing the neural stem cells to selectively become neurons or glial cells.

30 Claims, 1 Drawing Sheet

U.S. PATENT DOCUMENTS

| | | | |
|---|---|---|---|
| 6,239,105 | B1 | 5/2001 | Brewitt |
| 6,242,563 | B1 | 6/2001 | Dong |
| 6,294,346 | B1 | 9/2001 | Weiss et al. |
| 6,329,508 | B1 | 12/2001 | Friden |
| 6,333,031 | B1 | 12/2001 | Olsson et al. |
| 6,376,218 | B1 | 4/2002 | Hsu et al. |
| 6,395,546 | B1 * | 5/2002 | Zobel et al. ............ 435/377 |
| 6,399,316 | B1 | 6/2002 | Onda et al. |
| 6,413,952 | B1 | 7/2002 | Luengo et al. |
| 6,429,186 | B1 | 8/2002 | Fuh et al. |
| 6,551,618 | B2 | 4/2003 | Baird et al. |
| 6,618,698 | B1 | 9/2003 | Beausoleil et al. |
| 6,680,295 | B1 | 1/2004 | Arimura |
| 6,797,264 | B1 * | 9/2004 | Eriksson ............... 424/93.1 |
| 6,812,027 | B2 | 11/2004 | Goldman et al. |
| 7,048,934 | B2 | 5/2006 | Thompson et al. |
| 7,132,287 | B2 * | 11/2006 | Rajan et al. ............ 435/377 |
| 2002/0098178 | A1 | 7/2002 | Brand |
| 2003/0032181 | A1 | 2/2003 | Weiss et al. |
| 2003/0049838 | A1 | 3/2003 | Thompson et al. |
| 2003/0054551 | A1 | 3/2003 | Shingo et al. |
| 2003/0054998 | A1 | 3/2003 | Shingo et al. |
| 2004/0038888 | A1 | 2/2004 | Mercer et al. |
| 2004/0092448 | A1 | 5/2004 | Ohta et al. |
| 2004/0209000 | A1 | 10/2004 | Curtiss et al. |
| 2004/0209812 | A1 | 10/2004 | Renzi et al. |
| 2005/0009847 | A1 | 1/2005 | Bertilsson et al. |
| 2005/0245436 | A1 | 11/2005 | Weiss et al. |
| 2006/0089309 | A1 | 4/2006 | Tucker |
| 2006/0148084 | A1 | 7/2006 | Shingo et al. |
| 2007/0098698 | A1 | 5/2007 | Gregg et al. |
| 2007/0111932 | A1 | 5/2007 | Anderson |
| 2007/0179092 | A1 | 8/2007 | Ohta et al. |
| 2008/0039389 | A1 | 2/2008 | Weiss et al. |
| 2008/0181873 | A1 | 7/2008 | Shingo et al. |
| 2008/0286234 | A1 | 11/2008 | Eyink |

FOREIGN PATENT DOCUMENTS

| | | |
|---|---|---|
| CA | 2353553 | 6/2000 |
| CA | 2556266 | 8/2005 |
| EP | 0467279 A3 | 1/1992 |
| WO | WO 90 05185 | 5/1990 |
| WO | WO 93 01275 | 1/1993 |
| WO | WO 9409119 | 4/1994 |
| WO | WO 94 10292 | 5/1994 |
| WO | WO 96 09318 | 3/1996 |
| WO | WO 96/40231 | 12/1996 |
| WO | WO 97/48729 | 12/1997 |
| WO | WO 99/15191 | 4/1999 |
| WO | WO 99/21966 | 5/1999 |
| WO | WO 99 51272 | 10/1999 |
| WO | WO 00/05260 | 2/2000 |
| WO | WO 00/13650 | 3/2000 |
| WO | WO 00 30675 | 6/2000 |
| WO | WO0128574 | 4/2001 |
| WO | WO 03 018782 | 3/2003 |
| WO | WO 03 024472 | 3/2003 |
| WO | WO 03 035475 | 5/2003 |
| WO | WO 03 040310 | 5/2003 |
| WO | WO 03 092716 | 11/2003 |
| WO | WO 2007106987 | 9/2007 |

OTHER PUBLICATIONS

Lim et al., Neuron, vol. 28, Issue 3, Dec. 2000, pp. 713-726.*

Patil, A-A., "The Effect of Human Chorionic Gonadotropin (HCG) on Restoration of Physiological Contibuity of the Spinal Cord. A Preliminary Report" Int. Surg., Vol. 75, pp. 54-57, 1990.

Patil, A-A., "The Study of the Effect of Human Chorionic Gonadotrophic (HCG) Hormone on the Survival of Adrenal Medulla Transport in Brain. Preliminary Study" Acta Neurochirurgica, Vol. 87, pp. 76-78, 1987.

Patil, A-A. and Nagaraj, M.P., "The Effect of Human Chorionic Gonadotropin (HCG) on Functional Recovery of Spinal Cord Sectioned Rats*" Acta Neurochirurgica, Vol. 69, pp. 205-218, 1983.

Patil, A-A. and Nagaraj, M.P., Neurosurgery, Vol. 12, No. 5, pp. 593-594, 1983.

Arsenijevic et al., "Insulin-like growth factor-I is necessary for neural stem cell proliferation and demonstrates distinct actions of epidermal growth factor and fibroblast growth factor-2," Journal of Neuroscience, pp. 7194-7202 (2001).

Lobie et al., "Growth hormone, insulin-like growth factor I and the CNS: localization, function and mechanism of action," Growth Hormone & IGF Research, pp. S51-S56 (2000).

Bernichtein S., et al. (2001). S179D-human PRL, a pseudophosphorylated human PRL analog, is an agonist and not an antagonist. Endocrinology. 142(9):3950-3963.

Cerami, A., et al. (2001). Effects of epoetin alfa on the central nervous system. Semin Oncol. 28(2 Suppl 8):66-70.

DiCicco-Bloom, E., et al. (1998). The PACAP ligand/receptor system regulates cerebral cortical neurogenesis. Ann N Y Acad Sci. 865:274-289.

Fernandez-Pol, J.A. (1985). Epidermal growth factor receptor of A431 cells. Characterization of a monoclonal anti-receptor antibody noncompetitive agonist of epidermal growth factor action. J Biol Chem. 260(8):5003-5011.

Gage, F.H. (2000). Mammalian neural stem cells. Science. 287(5457):1433-1438.

Johnson, D.L., and Jolliffe, L.K. (2000). Erythropoietin mimetic peptides and the future. Nephrol Dial Transplant. 15(9):1274-1277.

Kandel, E.R., et al. (1991). Principles of Neural Science, p. 981.

Kaushansky, K. (2001). Hematopoietic growth factor mimetics. Ann N Y Acad Sci. 938:131-138.

Kolb, B., et al. (1997). Nerve growth factor treatment prevents dendritic atrophy and promotes recovery of function after cortical injury. Neuroscience. 76(4):1139-1151.

Konishi, Y., et al. (1993). Trophic effect of erythropoietin and other hematopoietic factors on central cholinergic neurons in vitro and in vivo. Brain Res. 609(1-2):29-35.

Lee, M., et al. (2001). Pituitary adenylyl cyclase-activating polypeptide stimulates DNA synthesis but delays maturation of oligodendrocyte progenitors. J Neurosci. 21(11):3849-3859.

Livnah, O., et al. (1996). Functional mimicry of a protein hormone by a peptide agonist: the EPO receptor complex at 2.8 A. Science. 273(5274):464-471.

Mode, A., et al. (1996). The human growth hormone (hGH) antagonist G120RhGH does not antagonize GH in the rat, but has paradoxical agonist activity, probably via the prolactin receptor. Endocrinology. 137(2):447-454.

Moro, O., Lerner, E.A. (1997). Maxadilan, the vasodilator from sand flies, is a specific pituitary adenylate cyclase activating peptide type I receptor agonist. J Biol Chem. 272(2):966-970.

Phelps, C.J., and Bartke, A. (1997). Stimulatory effect of human, but not bovine, growth hormone expression on numbers of tuberoinfundibular dopaminergic neurons in transgenic mice. Endocrinology. 138(7):2849-2855.

Phelps, C.J., and Hurley, D.L. (1999). Pituitary hormones as neurotrophic signals: update on hypothalamic differentiation in genetic models of altered feedback. Proc Soc Exp Biol Med. 222(1):39-58.

Rochefort, C., et al. (2002). Enriched odor exposure increases the number of newborn neurons in the adult olfactory bulb and improves odor memory. J Neurosci. 22(7):2679-2689.

Shimazaki, T., et al. (2001). The ciliary neurotrophic factor/leukemia inhibitory factor/gp130 receptor complex operates in the maintenance of mammalian forebrain neural stem cells. J Neurosci. 21(19):7642-7653.

Shingo, T., et al. (2001). Erythropoietin regulates the in vitro and in vivo production of neuronal progenitors by mammalian forebrain neural stem cells. J Neurosci. 21(24):9733-9743.

Sorokan, S.T., and Weiss, S. (1997). Erythropoietin mediates increased neurogenesis by embryonic CNS stem cells following a modest hypoxic insult. Soc for Neurosci Abstr 23(1/2):320.

Wrighton, N.C., et al. (1996). Small peptides as potent mimetics of the protein hormone erythropoietin. Science. 273(5274):458-464.

Aberg, M.A.I. et al. "Peripheral Infusion of IGF-I Selectively Induces Neurogenesis in the Adult Rat Hippocampus." J of Neuro., vol. 20, No. 8, pp. 2896-2903 (Apr. 15, 2000).

Abramsky, O. et al. "Suppressive Effect of Pregnancy on Ms and EAE" Prog. Clin. Biol. Res., pp. 399-406 (1984).

Allen, J.S. et al. "Sexual dimorphism and asymmetries in the gray-white composition of the human cerebrum" NeuroImage, vol. 18, pp. 880-894 (2003).

Anderson, M.F. et al. "Insulin-like growth factor-I and neurogenesis in the adult mammalian brain." Brain Res Dev Brain Res., vol. 134, No. 1-2, pp. 115-122 (Mar. 31, 2002).

Arimura, A. et al. "PACAP functions as a neurotrophic factor" Ann. NY Acad. Sci., vol. 739, pp. 228-243 (1994).

Arimura, A. et al. "Perspectives on pituitary adenylate cyclase activating polypeptide PACAP in the neuroendocrine, endocrine and nervous systems" Jap. J. Physiol., vol. 48, pp. 301-331 (1998).

Arimura, A. et al. "Tissue Distribution of PACAP as Determined by RIA: Highly Abundant in the Rat Brain Testes" , Endocrinol., Vol. 129, pp. 2787-2789 (1991).

Arimura, A. "Pituitary adenylate cyclase activating polypeptide PACAP: Discovery and current status of research" Regulatory Peptides, Vol. 37, pp. 287-303 (1992).

Armstrong, R.C. et al. "Absence of fibroblast growth factor 2 promotes oligodendroglial repopulation of demyelinated white matter" J Neurosci., vol. 22, No. 19, pp. 8574-8585 (2002).

Arnett, H.A. et al. "TNF-α promotes proliferation of oligodendrocyte progenitors and remyelination" Nature, vol. 4, pp. 1116-22 (2001).

Arsenijevic & Weiss "Insulin-like Growth Factor-I (IGF-I) Recruits a Distinct Population of Embryonic Neural Stem Cells, " Molecular Biology of the Cell, vol. 7 (Supp), p. 1842, (Dec. 1996).

Aston, C., et al. "Transcriptional profiling reveals evidence for signaling and oligodendroglial abnormalities in the temporal cortex from patients with major depressive disorder" Mol Psychiatry vol. 10, pp. 309-322 (2005).

Bambakidis, N. C. and Miller, R. H. "Transplantation of oligodendrocyte precursors and sonic hedgehog results in improved function and white matter sparing in the spinal cords of adult rats after contusion" J Spine, vol. 4, p. 16-26 (2004).

Banks, W.A. et al. "Passage of pituitary adenylate cyclase activating polypeptide 1-27 and pituitary adenylate cyclase activating polypeptide 1-38 across the blood-brain barrier" J. Pharmacol. Exp. Ther., vol. 267, No. 2, pp. 690-6 (1993).

Bartzokis, G.,, et al. "Heterogeneous age-related breakdown of white matter structural integrity: implications for cortical "disconnection" in aging and Alzheimer's disease" Neurobiol Aging, vol. 25, pp. 843-851 (2004).

Bayer, S.A. "Neuron production in the hippocampus and olfactory bulb of the adult rat brain: Addition or replacement?" Ann. NY Acad. Sci., vol. 457, pp. 163-73 (1985).

Bebo, Jr., B. F. and Dveksler, G. S. "Evidence that pregnancy specific glycoproteins regulate T-Cell function and inflammatory autoimmune disease during pregnancy" Curr. Drug Targets Inflamm. & Allergy. Vol. 4, pp. 231-237 (2005).

Bebo, Jr., B.F. et al. "Low-dose estrogen therapy ameliorates experimental autoimmune encephalomyelitis in two different inbred mouse strains" J. Immunol., vol. 166, pp. 2080-2089 (2001).

Brûck, W. and Stadelmann, C. "The spectrum of multiple sclerosis: new lessons from pathology" Curr Opin Neurol, vol. 18, pp. 221-224 (2005).

Buckner, R.L. "Memory and executive function in aging and AD: multiple factors that cause decline and reserve factors that compensate" Neuron, vol. 44, pp. 195-208 (2004).

Camarillo, I. G. et al. "Prolactin receptor expression in the epithelia and stroma of the rat mammary gland" Endocrinol, vol. 171, pp. 85-95 (2001).

Cao, Q. et al. "Functional recovery in traumatic spinal cord injury after transplantation of multineurotrophin-expressing glial-restricted precursor cells" J Neurosci, Vol. 25, No. 30, pp. 6947-6957 (2005).

Carey, R.G. et al. "Pituitary Adenylate Cyclase Activating Polypeptide Antimitogenic Signaling in Cerebral Cortical Progenitors is Regulated by p57Kip2-dependent CDK2 activity," J. Neurosci., vol. 22, No. 5, pp. 1583-91 (2002).

Cerghet, M. et al. "Proliferation and death of oligodendrocytes and myelin proteins are differentially regulated in male and female rodents" J Neurosci, vol. 26, No. 5, pp. 1439-1447 (2006).

Chikanza, I. C. "Prolactin and neuroimmunomodulation: in vitro and in vivo observations" Ann. N. Y. Acad. Sci., vol. 876, pp. 119-130 (1999).

Chojnacki, A. and Weiss, S. "Isolation of a novel platelet-derived growth factor-responsive precursor from the embryonic ventral forebrain" J. Neurosci., vol. 24, No. 48, pp. 10888-10899 (2004).

Christophe, J. "Type I Receptors for PACAP (a neuropeptide even more important than VIP?)" Biochim. Biophys. Acta, vol. 1154, pp. 183-99 (1993).

Confavreux, C. et al. Rate of pregnancy-related relapse in multiple sclerosis. N Engl J Med., vol. 339, No. 5, pp. 285-91 (1998).

Craig, C.G. et al. "In vivo growth factor expansion of endogenous subependymal neural precursor cell populations in adult mouse brain" J. Neurosci., vol. 16(8), pp. 2649-58 (1996).

Cunningham, B. C., et al. "High-resolution epitope mapping of hGH-receptor interactions by alanine-scanning mutagenesis", Sci., vol. 244, p. 4908 (1989).

Cunningham, B.C. et al. "Receptor and antibody epitopes in human growth hormone identified by homolog-scanning mutagenesis" Sci., vol. 243, No. 4896, pp. 1330-1336 (1989).

Dawson, M.R.L. et al. "NG2-expressing glial progenitor cells" an abundant and widespread population of cycling cells in the adult rat CNS Mol Cell Neurosci, vol. 24, pp. 476-488 (2003).

Devito, W.J., et al. "Prolactin induced expression of interleukin-1 alpha, tumor necrosis factoralpha, and transforming growth factor-alpha in cultured astrocytes", J. Cell Biochem. 57:290-298 (1995).

Dong, W. K. and Greenough W. T. "Plasticity of nonneuronal brain tissue: roles in developmental disorders" Ment Retard Dev Disabil Res. Rev., vol. 10, pp. 85-90 (2004).

Draca, S. and Levic, X. "The possible role of prolactin in the immunopathogenesis of multiple sclerosis" Med. Hypotheses, vol. 47, pp. 89-92 (1996).

Dubey, A.K. et al. "Differential Penetration of Three Anterior Pituitary Peptide Hormones into the cerebrospinal fluid of rhesus monkeys" Life Sci., vol. 32, Issue 16, pp. 1857-1863 (Apr. 18, 1983) abstract.

Faulkner, J. and Keirstead, H. S. "Human embryonic stem cell-derived oligodendrocyte progenitors for the treatment of spinal cord injury" Transpl. Immunol., vol. 15, pp. 131-142 (2005).

Ferro, J. M. and Madureira, S. "Age-related white matter changes and cognitive impairment" J Neurol Sci., Vols. 203-204, pp. 221-225 (2002).

Fields, R.D. "Myelination: an overlooked mechanism of synaptic plasticity?" Neuroscientist, vol. 11, pp. 528-531 (2005).

Fleming, A. S. and Walsh, C. "Neuropsychology of maternal behavior in the rat: c-fos expression during mother-litter interactions" Psychoneuroendocrinology Vol. 19, Nos. 5-7, pp. 429-443 (1994).

Freed, C.R. et al. "Survival of Implanted Fetal Dopamine Cells and Neurologic Improvement 12 to 46 Months After Transplantation for Parkinson Disease", N. Engl. J. Med., Vol. 327, No. 22, pp. 1549-1555 (1992).

Freeman, M.E., et al., "Prolactin: structure, function and regulation of secretion", Physiol. Rev. 80: 1523-1631 (2000).

Gage, F.H. et al. "Isolation, characterization, and use of stem cells from the CNS." Annu Rev Neurosci., Vol. 18, pp. 159-192 (1995).

Gage, F.H. et al. "Survival and differentiation of adult neuronal progenitor cells transplanted to the adult brain." Proc Natl Acad Sci., vol. 92, pp. 11879-11883 (Dec. 5, 1995).

Gatewood, J. D. et al., "Motherhood mitigates aging-related decrements in learning and memory and positively affects brain aging in the rat" Brain Res Bull, vol. 66, pp. 91-98 (2005).

Gensert, J. M. and Goldman J. E., "In vivo characterization of endogenous proliferating cells in adult rat subcortical white matter" GLIA, Vol. 17, pp. 39-51 (1996).

Gensert, J. M. and Goldman, J. E. "Endogenous progenitors remyelinate demyelinated axons in the adult CNS" Neuron, vol. 19, pp. 197-203 (1997).

Goeddeli, D.V., et al. Direct expression in *Escherichia coli* of a DNA sequence coding for human growth hormone. Nature, vol. 281, No. 5732, pp. 544-548 (1979).

Gray, G.L., et al. Periplasmic production of correctly processed human growth hormone in *Escherichia coli*: natural and bacterial signal sequences are interchangeable. Gene, vol. 39, Nos. 2-3, pp. 247-254 (1985).

Gur, R. C. et al. "Sex differences in brain gray and white matter in healthy young adults: correlations with cognitive performance" J Neurosci, vol. 19, No. 10, pp. 4065-4072 (1999).

Hack, M. A. et al. "Neuronal fate determinants of adult olfactory bulb neurogenesis" Nat Neurosci,. vol. 8, No. 7, pp. 865-872 (2005).

Haier, R.J. et al. "The neuroanatomy of general intelligence: sex matters" Neuroimage vol. 25, pp. 320-327 (2005).

Hansel, D.E. et al., "Regulation of Olfactory Neurogenesis by Amidated Neuropeptides,", J. Neurosci. Res. vol. 66, pp. 1-7 (2001).

Hashimoto, H. et al. "Altered Psychomotor Behaviors in Mice Lacking Pituitary Adenylate Cyclase-Activating Polypeptide (PACAP)", PNAS, vol. 98, No. 23, pp. 13355-13360 (2001).

Hashimoto H. et al. "Molecular Cloning and Tissue Distribution of a Receptor for Pituitary Adenylate Cyclase Activating Polypeptide", Neuron 11:333-342 (1993).

Hirose, M. et al. "Gene expression of PACAP and its receptors in the ES cell-derived neuronal stem cells." Japanese Journal of Pharmacology, The Japanese Pharmacological Society, Kyoto, JP, vol. 88, Suppl. 1, p. 143.

Inzitari, D. "Leukoaraiosis: An independent risk factor for stroke?" Stroke, Vol. 34, pp. 2067-2071 (2003).

Ito, A. et al. "Estrogen treatment down-regulates TNF-α production and reduces the severity of experimental autoimmune encephalomyelitis in cytokine knockout mice" J Immunol, vol. 167, pp. 542-552 (2001).

Jokinen, H. et al. "Medial temporal lobe atrophy and memory deficits in elderly stroke patients" Eur J Neurol 11:825-832 (2004).

Kaplan, M.S. "Neurogenesis in the 3-month Old Rat Visual Cortex" J. Comp. Neurol., vol. 195, pp. 323-338 (1981).

Karimi-Abdolrezaee, S. et al., "Delayed transplantation of adult neural precursor cells promotes remyelination and functional neurological recovery after spinal cord injury" J Neurosci., vol. 26, No. 13, pp. 3377-3389 (2006).

Keirstead, H.S. et al. "Human embryonic stem cell-derived oligodendrocyte progenitor cell transplants remyelinate and restore locomotion after spinal cord injury" J Neurosci., vol. 25, No. 19, pp. 4694-4075 (2005).

Kieseier, B.C. et al. "Multiple sclerosis-novel insights and new therapeutic strategies" Curr Opin Neurol., vol. 18, pp. 211-220 (2005).

Kim, J. H. and Juraska, J. M. "Sex differences in the development of axon number in the splenium of the rat corpus callosum from postnatal day 15 through 60" Brain Res. Dev. Brain Res., vol. 102, p. 77-85 (1997).

Kim, S. et al. "Estriol ameliorates autoimmune demyelinating disease: implications for multiple sclerosis" Neurology, vol. 52, pp. 1230-1238 (1999).

Kimura, C. et al. "A Novel Peptide Which Stimulates Adenylate Cyclase: Molecular Cloning and Characterization of the Ovine and Human cDNAs," Biochem. Biophys. Res. Comm., vol. 166, pp. 81-89 (1990).

Kinsley, C. H. et al. "Motherhood improves learning and memory" Nature, vol. 402, p. 137 (1999).

Kovacs, T. et al. "Olfactory Bulb in Multiple System Atrophy", Movement Disorder, vol. 18, No. 8, pp. 938-942 (2003).

Lambert, K. G. et al. "Pup exposure differentially enhances foraging ability in primiparous and nulliparous rats" Physiol. Behav., vol. 84, pp. 799-806 (2005).

Learish, R.D. et al. "Intraventricular transplantation of oligodendrocyte progenitors into a fetal myelin mutant results in widespread formation of myelin" Ann Neurol, vol. 46, pp. 716-722 (1999).

Lee, K. H. et al. "Effects of glial transplantation on functional recovery following acute spinal cord injury" J. Neurotrauma, vol. 22, No. 5, 575-589, (2005).

Lelievre, V. et al. "Cross-talk between PACAP and sonic hedgehog (SHH) pathways in neural stem cells, cerebellar granular progenitor cells and oligodendrocyte progenitors to control cell fate and proliferation." Regulatory Peptides, vol. 115, No. 1, p. 50 (2003) (abstract).

Lelievre, V. et al. "Fibroblast growth factor-2 converts PACAP growth action on embryonic hindbrain precursors from stimulation to inhibition." Journal of Neuroscience Research, vol. 67, No. 5, pp. 566-573 (Mar. 1, 2002).

Lelievre, V. et al. "Interactive of PACAP with sonic Hedgehog on neural stem cell and oligodendrocyte progenitor proliferation." J of Neurochemistry, vol. 85, Supp 1, p. 66 (May 20, 2003).

Levine, J. M. et al. "The oligodendrocyte precursor cell in health and disease" Trends Neurosci., vol. 24, No. 1, pp. 39-47 (2001).

Levison, S.W. et al. "Cycling cells in the adult rat neocortex preferentially generate oligodendroglia" J Neurosci Res., vol. 57, pp. 435-466 (1999).

Lim, D.A., et al. "Noggin antagonizes BMP signaling to create a niche for adult neurogenesis", Neuron, Vol. 28, pp. 713-726 (2000).

Lindholm et al. "Developmental Regulation of Pituitary Adenylate Cyclase Activating Polypeptide (PACAP) and its Receptor 1 in Rat Brain: Function of PACAP as a Neurotrophic Factor," Ann. N.Y. Acad. Sci., vol. 865, pp. 189-196 (1998).

Lledo, P. M. et al. "Adult neurogenesis and functional plasticity in neuronal circuits" Nat Rev Neurosci, vol. 7, pp. 179-193 (2006).

Love, G. et al. "Maternal experience produces long-lasting behavioral modification in the rat" Behav Neurosci., vol. 119, No. 4, pp. 1084-1096 (2005).

Lowman, H.B. et al. "Mutational analysis and protein engineering of receptor-binding determinants in human placental lactogen" J. Biol. Chemistry, vol. 266(17), pp. 10982-10988 (1991).

Lu, N. et al. "Pituitary Adenylate Cyclase-Activating Polypeptide is an Autocrine Inhibitor of Mitosis in cultured Cortical Precursor Cells," Proc. Natl. Acad. Sci., vol. 94, pp. 3357-3362 (1997).

Lubetzki, C. et al. "Promoting repair in multiple sclerosis: problems and prospects" Curr Opin Neurol., Vol. 18, pp. 237-244 (2005).

Lyoo, I.K. et al. "White matter hyperintensities on magnetic resonance imaging of the brain in children with psychiatric disorders" Compr Psychiatry, vol. 43, No. 5, pp. 361-368 (2002).

Mack, C. M. et al. "Sex differences in the distribution of axon types within the genu of the rat corpus callosum" Brain Res, vol. 697, pp. 152-156.

Menn, B. et al. "Origin of oligodendrocytes in the subventricular zone of the adult brain" J Neurosci., vol. 26, No. 30, pp. 7907-7918 (2006).

Miyata, A. et al. "Isolation of a Novel 38 Residue-Hypothalamic Polypeptide which Stimulates Adenylate Cyclase in Pituitary Cells." Biochem. Bophys. Res. Comm. 164:567-574 (1989).

Moore, P.B. et al. "Cerebral white matter lesions in bipolar affective disorder: relationship to outcome" Br J Psychiatry, vol. 178, pp. 172-176 (2001).

Mori, E. "Impact of subcortical ischemic lesions on behavior and cognition" Ann. N. Y. Acad Sci., vol. 977, p. 141-148 (2002).

Mulloy, A.L. et al. "Absorption of orally administered bovine prolactin by neonatal rats" Biol. Neonate, vol. 36, No. 3-4, pp. 148-153, (1979) abstract.

Nait-Oumesmar, B. et al. "Progenitor cells of the adult mouse subventricular zone proliferate, migrate and differentiate into oligodendrocytes after demyelination" Eur J Neurosci., vol. 11, pp. 4357-4366 (1999).

Neumann, I. D. "Alterations in behavioral and neuroendocrine stress coping strategies in pregnant, parturient and lactating rats" Prog. Brain Res., vol. 133, pp. 143-152 (2001).

Nicot, A et al. "Regulation of Neuroblast Mitosis is Determined by PACAP Receptor Isoform Expression", PNAS, vol. 98, No. 8, pp. 4758-4763 (2001).

Nuñez, J. L. et al. "Myelination in the splenium of the *Corpus callosum* in adult male and female rats" Dev Brain Res., vol. 120, pp. 87-90 (2000).

Nyberg, F. "Aging effects on growth hormone receptor binding in the brain", Exp. Gerontol, vol. 32, No. 4-5, pp. 521-528 (1997).

Nyberg, F. "Growth hormone in the brain: characteristics of specific brain targets for the hormone and their functional significance", Front Neuroendocrinol., vol. 21, pp. 330-348 (2000).

Ohta S. and Weiss, S. "Pituitary adenylate cylase-activating polypeptide (PACAP) regulates forebrain neural stem cell fate in vitro and in vivo." Society for Neuroscience Abstract Viewer and Itinerary Planner, vol. 329, No. 13, 2002 (abstract).

Ormandy, C. J. et al. "Null mutation of the prolactin receptor gene produces multiple reproductive defects in the mouse" Genes Dev., vol. 11, pp. 167-178 (1997).

Otto, C. et al., "Altered Emotional Behavior in PACAP-type-I-receptor-deficient Mice," Brain Res. Mol. Brain Res. 91(1-2):78-84 (2001).

Perlow et al. "Brain Grafts Reduce Motor Abnormalities Produced by Destruction of Nigrostriatal Dopamine System," Sci., vol. 204, pp. 643-647 (1979).

Pesce, M. et al. "Pituitary adenylate cyclass-activating polypeptide (PACAP) stimulates adenylate cyclase and promotes proliferation of mouse primordial germ cells." Development (Cambridge), vol. 122, No. 1, pp. 215-221 (1996).

Peters, A. and Sethares C. "Oligodendrocytes, their progenitors and other neuroglial cells in the aging primate cerebral cortex" Cereb Cortex, vol. 14, pp. 995-1007 (2004).

Peters, A. et al., "Effects of aging on the neuroglial cells and pericytes within area 17 of the rhesus monkey cerebral cortex" Anat Rec, vol. 229, pp. 384-398 (1991).

Peters, A. J. "The effects of normal aging on myelin and nerve fibers: a review" J Neurocytol, vol. 31, pp. 581-593 (2002).

Picard-Riera, N. et al. "Experimental autoimmune encephalomyelitis mobilizes neural progenitors from the subventricular zone to undergo oligodendrogenesis in adult mice" PNAS, vol. 99, No. 20, pp. 13211-13216 (2002).

Polito, A. and Reynolds, R. "NG2 expressing cells as oligodendrocyte progenitors in the normal and demyelinated adult central nervous system" Anat., vol. 207, pp. 707-716 (2005).

Potten, C.S. and Loeffler, M. "Stem Cells: Attributes, Cycles, Spirals, Pitfalls and Uncertainties. Lessons for and from the Crypt," Development, vol. 110, pp. 1001-1020 (1990).

Rakic, "Limits of Neurogenesis in Primates," Science 227:1054-1056 (1985).

Rawlings, S.R. "At the Cutting Edge PACAP, PACAP Receptors, and Intracellular Signalling", Mol. and Cellular Endocrinol., vol. 191, pp. C5-C9 (1994).

Reynolds, B.A. and Weiss, S. "Generation of Neurons and Astrocytes from Isolated Cells of the Adult Mammalian Central Nervous System," Sci., vol. 255, pp. 1707-1710 (1992).

Rietze et al. "Mitotically Active Cells that Generate Neurons and Astrocytes are Present in Multiple Regions of the Adult Mouse Hippocampus," J. Comp. Neurol., Vol. 424, No. 3, pp. 397-408 (2000).

Rostene, W. et al. "VIP and PAGAP via G-Protein coupled receptors are potent inducers of mouse embryonic stem cell neuronal differentiation." Regulatory Peptides, vol. 115, No. 1, p. 55. (2003).

Scheepens, A. et al. "Growth Hormone as a Neuronal Rescue Factor During Recovery from CNS Injury." Neuroscience, vol. 104, No. 3, pp. 677-687 (Jun. 14, 2001).

Schlessinger, J. et al. "Crystal Structure of a Ternary FGF-FGFR-Heparin Complex Reveals a Dual Role for Heparin in FGFR Binding Dimerization" Molecular Cell, Vol. 6, No. 3, pp. 743-750 (Sep. 2000).

Schradin, C. and Anzenberger G. "Prolactin, the Hormone of Paternity" News Physiol Sci., vol. 14, pp. 223-231 (1999).

Scolding, N. J. and Franklin, R. J. M. "Remyelination in demyelinating disease" Baillieres Clin Neurol., vol. 6(3), pp. 525-548 (1997).

Shingo, T. et al. "Pregnancy-stimulated neurogenesis in the adult female forebrain mediated by prolactin" Sci., vol. 299, pp. 117-120 (2003).

Shioda, J. et al. "Pleiotropic functions of PACAP in the CNS. Neuroprotection and neurodevelopment" Ann. NY Acad. Sci., vol. 1070, pp. 550-560 (2006).

Sicotte, N. L. et al. "Treatment of multiple sclerosis with the pregnancy hormone estriol" Ann Neurol., vol. 52, pp. 421-428 (2002).

Silverstone, T. et al. "Deep white matter hyperintensities in patients with bipolar depression, unipolar depression and age-matched control subjects" Bipolar Disord, vol. 5, pp. 53-57 (2003).

Sirevaag, A. M. and Greenough, W. T. "Differential rearing effects on rat visual cortex synapses. III. Neuronal and glial nuclei, boutons, dendrites and capillaries" Brain Res., vol. 424, pp. 320-332 (1987).

Spencer, D.D. et al. "Unilateral Transplantation of Human Fetal Mesencephalic Tissue into the Caudate Nucleus of Patients with Parkinson's Disease," New Engl. J. Med., vol. 327, No. 22, pp. 1541-1548 (1992).

Stangel, M. and Hartung H-P. "Remyelinating strategies for the treatment of multiple sclerosis" Prog Neurobiol., vol. 68, pp. 361-376 (2002).

Stevens, B. et al, "Adenosine: a neuron-glial transmitter promoting myelination in the CNS in response to action potentials" Neuron, vol. 36, pp. 855-868 (2002).

Studer L. et al. "Enhanced Proliferation, Survival, and Dopaminergic Differentiation of CNS Precursors in Lowered Oxygen" J. Neurosci., Vol. 201, No. 19, pp. 7377-7383 (Oct. 1, 2000).

Sturrock, R. R. "Myelination of the mouse *Corpus callosum*" Neuropathol Appl Neurobiol., vol. 6, pp. 415-420 (1980).

Szeligo, F. and Leblond, C. P. "Response of the three main types of glial cells of cortex and *Corpus callosum* in rats handled during suckling or exposed to enriched, control and impoverished environments following weaning" J. Comp. Neurol., vol. 172, pp. 247-263 (1977).

Tang, D. G. et al. "Long-term culture of purified postnatal oligodendrocyte presursor cells. Evidence for an intrinsic maturation program that plays out over months" J. Cell Biol., vol. 148, pp. 971-984 (2000).

Tauber, H. et al. "Myelination in rabbit optic nerves is accelerated by artificial eye opening" Neuroci Lett., vol. 16, pp. 235-238 (1980).

The American Heritage Dictionary of the English Language 4th Ed., Dictionary.com/neural (2000).

Totoiu, M. O. and Keirstead, H. S. "Spinal cord injury is accompanied by chronic progressive demyelination" J Comp Neurol., Vol. 486, pp. 373-383 (2005).

Tropepe, V. et al., "Transforming growth factor-α null and senescent mice show decreased neural progenitor cell proliferation in the forebrain subependyma", J. Neurosci., vol. 17, Issue 20, pp. 7850-7859 (1997).

Van Der Kooy and Weiss, "Why Stem Cells?", Sci. vol. 287, pp. 1439-1441 (2000).

Van Walderveen et al. "Magnetic resonance evaluation of disease activity during pregnancy in multiple sclerosis" Neurology, vol. 44, pp. 327-329 (1994).

Vaudry, D. et al. "Neurotrophic activity of pituitary adenylate cyclase-activating polypeptide on rate cerebellar cortex during development." Proc. of the Nat. Aca. of Sci., vol. 96, No. 16, pp. 9415-9420 (Aug. 3, 1999).

Vaudry, D. et al. "Pituitary adenylate cyclase-activating polypeptide and its receptors from structure to functions," Pharmacol. Rev., vol. 52, No. 2, pp. 269-324 (2000).

Voskuhl, R. R. "Hormone-based therapies in MS" Int. MS J, Vol. 10, pp. 60-66 (2003).

Walker, C. D. et al., "Mother to infant or infant to mother? Reciprocal regulation of responsiveness to stress in rodents and the implications for humans" J. Psy. Neurosci. vol. 29, No. 5, pp. 364-382 (2004).

Wardlaw, J.M. et al "Is diffusion imaging appearance an independent predictor of outcome after ischemic stroke?" Neurology, vol. 59, pp. 1381-1387 (2002).

Waschek, J.A. "Multiple actions of pituitary adenylyl cyclase activating peptide in nervous system development and regeneration" Develop. Neuro., Viol. 24, pp. 14-23, (2002).

Waschek, J.A. "VIP and PACAP Receptor-mediated actions on cell proliferation and survival," Ann. N.Y. Acad. Sci., Vol. 805, pp. 290-301 (1996).

Weetman A. P. "The immunology of pregnancy" Thyroid, vol. 9, No. 7, pp. 643-646 (1999).

Whittemore S.R., et al. "Mitogen and substrate differentially affect the lineage restriction of adult rat subventricular zone neural precursor cell populations" Exp. Cell. Res., vol. 252, No. 1, pp. 75-95 (Oct. 10, 1992).

Widner, H. et al. "Bilateral fetal Mesencephalic grafting into two patients with parkinsonism induced by I-methyl-4-phenyl-1,2,3,6-tetrahydropyridine (MPTP)," N. Engl. J. Med. vol. 327, pp. 1556-1563 (1992).

Wu, H. Y. et al. "Expression of QKI proteins and MAP1B identifies actively myelinating oligodendrocytes in adult rat brain" Mol. Cell. Neurosci., vol. 17, pp. 292-302 (2001).

Yuhara et al., "PACAP has a Neurotrophic effect on cultured basal forebrain cholinergic neurons from adult rats," Dev. Brain Res., vol. 131, No. 1, pp. 41-50 (2001).

Al-Hader, A. A. et al., "Neurons from fetal rat brain contains functional luteinizing hormone/chorionic gonadotropin receptors," Bio. of Reprod., vol. 56, pp. 1071-1076, (1997).

Al-Hader, A. A. et al., "Novel expression of functional luteinizing hormone/chorionic gonadotropin receptors in cultured glial cells from neonatal rat brains," Bio. of Reprod., vol. 56, pp. 501-507 (1997).

Arlotta P. et al, "Introduction to Adult Neurogensis," Annals of the N.Y. Acad. of Sci., vol. 991, No. 1, pp. 229-236 (2003).

Bithell A., "Neural Stem Cells and Replacement Therapy: Making the right cells," Clin. Sci., vol. 108, pp. 13-22 (2003).

Brown, J. "Enriched environment and physical activity stimulate hippocampal but not olfactory bulb neurogenesis," Eur J Neurosci. vol. 17, No. 10, pp. 2042-2046 (2003).

Craig, C.G. et al., "In vivo growth factor expansion of endogenous subependymal neural precursor cell populations in the adult mouse brain," J Neurosci. vol. 16, No. 8, pp. 2649-2658 (1996).

Curtis, M.A., "Neurogenisis in the diseased adult human brain," Cell Cycle, vol. 2, No. 5, pp. 428-430 (2003).

Dulac C. and Torello A.T.T. "Molecular detection of pheromone signals in mammals: from genes to behaviour," Nat. Rev. Neurosci., vol. 4, No. 7, pp. 551-562 (2003).

Fowler C.D., et al., "The effects of social environment on adult neurogenesis in the female prairie vole," J. Neurobiology, vol. 51, No. 2, pp. 115-128 (2002).

Frisen, J. et al., "Central nervous system stem cells in the embryo and adult," Cell Mol Life Sci. vol. 54, No. 9, pp. 935-945 (1998).

Goffin V. et al., "Sequence-Function Relationships within the Expanding Family of Prolactin, Growth Hormone, Placental Lactogen, and Related Proteins in Mammals," Endo. Reviews, vol. 17, No. 4, pp. 385-410 (2007).

Huhtaniemi, I. et al., "Transgenic and knockout mouse models for the study of luteinizing hormone and luteinizing hormone receptor function," Mol Cell Endocrinol. 187(1-2):49-56 (2002).

Johnson, D. L., and Jolliffe, L.K., "Erythropoietin mimetic peptides and the future," Nephrol: Dial. Transplant., vol. 15, No. 9, pp. 1274-1277 (2000).

Karbanova, J. et al., Neural stem cells transplanted into intact brains as neurospheres form solid grafts composed of neurons, astrocytes and oligodendrocyte precursors, Biomed. Papers 148(2):217-220 (2004).

Kaushansky, K., "Hematopoietic growth factor mimetics," Ann. N.Y. Acad. Sci., Vol. 938, pp. 131-138 (2001).

Kempermann, G., and Gage, F.H. "Experience-dependent regulation of adult hippocampal neurogenesis: effects of long-term stimulation and stimulus withdrawal," Hippocampus, vol. 9, No. 3, pp. 321-332 (1999).

Kiyokawa, Y. et al., "Modulatory role of testosterone in alarm pheromone release by male rats," Horm. Behav., vol. 45, No. 2, pp. 122-127 (2004).

Lei, Z.M. et al., "Neural actions of luteinizing hormone and human chorionic gonadotropin," Seminars in Reprod. Med., vol. 19, No. 1., pp. 103-109 (2001).

Lushkin, M.B., "Restricted proliferation and migration of postnatally generated neurons derived from the forebrain subventricular zone," Neuron vol. 11, No. 1, pp. 173-189 (1993).

Ma, W. et al., "Role of the adrenal gland and adrenal-mediated chemosignals in suppression of estrus in the house mouse: The lee-boot effect revisited," Biol Reprod. vol. 59, No. 6, pp. 1317-1320 (1998).

Menezes, J.R. et al., "The division of neuronal progenitor cells during migration in the neonatal mammalian forebrain," Mol Cell Neurosci., vol. 6, No. 6, pp. 496-508 (1995).

Mode, A. et al., "The human growth hormone (hGH) antagonist$^{G120R}$ hGH does not antagonize GH in the rat, but has paradoxical agonist activity, probably via the prolactin receptor," Endocr. vol. 137, No. 2, pp. 447-454 (1996).

Moderschem, T.A.E. et al., "Prolactin is Involved in Glial Responses Following a Focal Injury to the Juvenile Rat Brain," Neurosci., vol. 145, pp. 963-973 (2007).

Moro, O. and Lerner E.A., "Maxadilan, the vasodilator from sand flies, is a specific pituitary adenylate cyclase activating peptide type I receptor agonist," J. Biol. Chem., vol. 272, No. 2, pp. 966-970 (1997).

Morrison, S.J. et al., "Regulatory mechanisms in stem cell biology," Cell, vol. 88, pp. 287-298, 1997.

Morshead, C.M. and Van Der Kooy, D. "Postmitotic death is the fate of constitutively proliferating cells in the subependymal layer of the adult mouse brain," J Neurosci., vol. 12, No. 1, pp. 249-256 (1992).

Nilsson, M. et al., "Enriched environment increased neurogenesis in the adult rat dentate gyrus and improves spatial memory," J Neurobiol., vol. 39, No. 4, pp. 569-578 (1999).

Ostenfeld T. and Svendsen C.N. et al, "Recent Advances in Stem Cell Neurobiology," Adv Tech Stand Neurosurg, vol. 28, pp. 3-89 (2003).

Park, K.I., "Transplantation of neural stem cells: cellular & gene therapy for hypoxic-ischemic brain injury," Yonsei Med J., vol. 41, No. 6, pp. 825-835 (2000).

Parker M.A., et al, "Expression profile of an operationally-defined neural stem cell clone," Exper. Neuro, vol. 194. pp. 320-332 (2005).

Peretto, P. et al., "The subependymal layer in rodents: a site of structural plasticity and cell migration in the adult mammalian brain" Brain Res Bull., vol. 49, No. 4, pp. 221-243 (1999).

Perlow, M.J. et al., "Brain grafts reduce motor abnormalities produced by destruction of nigrostriatal dopamine system," Sci., vol. 204, No. 4393, pp. 643-647 (1979).

Rao, M.S., "Multipotent and restricted precursors in the central nervous system," Anat. Rec. vol. 257, No. 4, pp. 137-148 (1999).

Reynolds, B.A. and Weiss, S., "Generation of neurons and astrocytes from isolated cells of the adult mammalian central nervous system," Sci., vol. 255, No. 5052, pp. 1707-1710 (1992).

Reynolds, B.A., and Weiss, S. "Clonal and population analyses demonstrate that an EGF-responsive mammalian embryonic CNS precursor is a stem cell," Develop. Bio., vol. 175, pp. 1-13 (1996).

Reynolds, J.N. et al., "Ethanol modulation of GABA receptor-activated Cl-currents in neurons of the chick, rat and mouse central nervous system," Eur J Pharmacol., vol. 224, No. 2-3, pp. 173-181 (1992).

Rochefort, C. et al., "Enriched odor Exposure increases the number of newborn neurons in the adult olfactory bulb and improves odor memory," J Neurosci., vol. 22, No. 7, pp. 2679-2689 (2002).

Rodriguez-Peña, A., "Oligodendrocyte development and thyroid hormone," J Neurobiol., vol. 40, No. 4, pp. 497-512 (1999).

Shingo, T. et al., "Pregancy-Stimulated Neurogenesis in the Adult Female Forebrain Mediated by Prolactin," Sci., vol. 229, pp. 117-120 (2003) (including Supporting Online Material (1-10 pages)).

Shingo, T. et al., "Erythropoietin regulates the in vitro and in vivo production of neuronal progenitors by mammalian forebrain neural stem cells," J Neurosci., vol. 21, No. 24, pp. 9733-9743 (2001).

Tanapat, P. et al., "Estrogen stimulates a transient increase in the number of new neurons in the dentate grus of the adult female rat," J Neurosci., vol. 19, No. 14, pp. 5792-5801 (1999).

Weiss, S. et al., "Is there a neural stem cell in the mammalian forebrain?" Trends Neuro., vol. 19, pp. 387-393 (1996).

Wrighton, N.C. et al., "Small peptides as potent mimetics of the protein hormone erythropoietin," Sci., vol. 273, No. 5274, pp. 458-463 (1996).

Zhang, F.P. et al., "Normal prenatal but arrested postnatal sexual development of luteinizing hormone receptor knockout (LuRKO) mice," Mol. Endocrinol., Vol. 15, No. 1, pp. 172-183 (2007).

Zhang, J.X. et al., "Scent, social status, and reproductive condition in rat-like hamsters (cricetulustriton)," Physiol Behav., vol. 74, No. 4-5, pp. 415-420 (2001).

Jin et al., "Alzheimer's disease drugs promote neurogenesis," Brain Research, 1085(1): 183-188, 2006.

Johnson et al., Evaluating the Role of the Hormone Prolactin in Neuroinflammation and repair associated with exerimental autoimmune encephalomyelitis; EndMS Research Conference, Banff, Alberta Canada,; Dec. 10-13, 2007.

Kolb et al, "Growth factor-stimulated generation of new cortical tissue and functional recovery after storke damage to the motor cortex of rats," J Cerebral Blood Flow & Metabolism, Sept. 20: 1-15, 2006.

Misra et al, J Pharm Pharmaceutic Sci., 6(2): 252-273, 2003.

Pluchino et al, Nature Vol 422(6933):688-694, 2003.

Schanzer et al, "Direct Stimulation of Adult Neural Stem Cells in vitro and Neurogenesis in vivo by vascular Endothelial Growth Factor," Brain Path 14(3):237-248, 2004.

Scharfman et al, "Increased neurogenesis and the ectopic granuae cells after intrahippocampal BDNF infusion in rats," Exp. Neuro, 192(2):348-356, 2005.

Shingo et al., Supporting Online Material pp. 1-10, "Pregnancy-Stimulated Neurogenesis in the Adult Female Forebrain Mediated by Prolactin" Science 299:117-20 (2003).

Tanaka R, "Potential of Use of Neural Stem Cells as Stroke as a Clinical Treatment," Juniendo Medical Journal, 52(1):2-10, 2006.

Van Dam et al, "Growth Hormone, insulin-like growth factor I and cognitive function in adults" Growth Horm IGF Res. 10 Supp B: S69-73, 2000.

Torner et al. "Prolactin Prevents Chronic Stress-Induced Decrease of Adult Hippocampal Neurogenesis and Promotes Neuronal Fate." *The Journal of Neuroscience*. 29(6): 1826-1833. Feb. 11, 2009.

* cited by examiner

FIGURE 1

COMBINED REGULATION OF NEURAL CELL PRODUCTION

RELATED APPLICATIONS

This application is a continuation of U.S. application Ser. No. 10/231,493, filed Aug. 30, 2002, which claims the benefit of U.S. Provisional Applications Ser. No. 60/316,365, filed Aug. 30, 2001; Ser. No. 60/316,579, filed Aug. 31, 2001; Ser. No. 60/322,514, filed Sep. 14, 2001; and Ser. No. 60/386,404, filed Jun. 7, 2002. The entire disclosure of each of these priority applications is hereby incorporated by reference.

FIELD OF THE INVENTION

This invention relates to a method of selectively producing neural cells, such as neurons or glial cells, in vitro or in vivo. Also provided are methods of treating or ameliorating neurodegenerative disease or medical conditions by producing neural cells.

REFERENCES

U.S. Patent Application Publication No. 2002 0098178 A1.
U.S. Pat. No. 5,023,252.
U.S. Pat. No. 5,128,242.
U.S. Pat. No. 5,198,542.
U.S. Pat. No. 5,208,320.
U.S. Pat. No. 5,268,164.
U.S. Pat. No. 5,326,860.
U.S. Pat. No. 5,506,107.
U.S. Pat. No. 5,506,206.
U.S. Pat. No. 5,527,527.
U.S. Pat. No. 5,547,935.
U.S. Pat. No. 5,614,184.
U.S. Pat. No. 5,623,050.
U.S. Pat. No. 5,686,416.
U.S. Pat. No. 5,723,115.
U.S. Pat. No. 5,750,376.
U.S. Pat. No. 5,773,569.
U.S. Pat. No. 5,801,147.
U.S. Pat. No. 5,833,988.
U.S. Pat. No. 5,837,460.
U.S. Pat. No. 5,851,832.
U.S. Pat. No. 5,885,574.
U.S. Pat. No. 5,955,346.
U.S. Pat. No. 5,977,307.
U.S. Pat. No. 5,980,885.
U.S. Pat. No. 6,015,555.
U.S. Pat. No. 6,048,971.
U.S. Pat. No. 6,191,106.
U.S. Pat. No. 6,242,563.
U.S. Pat. No. 6,329,508.
U.S. Pat. No. 6,333,031.
U.S. Pat. No. 6,413,952.
U.S. Pat. No. 6,429,186.
WO 96 40231.
WO 97 48729.

Bernichtein, S., et al. S179D-human PRL, a pseudophosphorylated human PRL analog, is an agonist and not an antagonist. Endocrinology 142(9):3950-3963 (2001).

Fernandez-Pol, J. A. Epidermal growth factor receptor of A431 cells. Characterization of a monoclonal anti-receptor antibody noncompetitive agonist of epidermal growth factor action. J. Biol. Chem. 260(8):5003-5011 (1985).

Johnson, D. L., et al. Erythropoietin mimetic peptides and the future. Nephrol. Dial. Transplant. 15(9):1274-1277 (2000).

Kaushansky, K. Hematopoietic growth factor mimetics. Ann. N.Y. Acad. Sci. 938:131-138 (2001).

Kolb, B., et al. Nerve growth factor treatment prevents dendritic atrophy and promotes recovery of function after cortical injury. Neuroscience 76(4):1139-1151 (1997).

Livnah, O., et al. Functional mimicry of a protein hormone by a peptide agonist: the EPO receptor complex at 2.8 A. Science 273(5274):464-471 (1996).

Mode, A., et al. The human growth hormone (hGH) antagonist G120RhGH does not antagonize GH in the rat, but has paradoxical agonist activity, probably via the prolactin receptor. Endocrinology 137(2):447-454 (1996).

Moro, O., et al. Maxadilan, the vasodilator from sand flies, is a specific pituitary adenylate cyclase activating peptide type I receptor agonist. J. Biol. Chem. 272(2):966-70 (1997).

Rochefort, C., et al. Enriched odor exposure increases the number of newborn neurons in the adult olfactory bulb and improves odor memory. J. Neurosci. 22(7):2679-2689 (2002).

Shimazaki, T., et al. The ciliary neurotrophic factor/leukemia inhibitory factor/gp130 receptor complex operates in the maintenance of mammalian forebrain neural stem cells. J. Neurosci. 21(19):7642-7653 (2001).

Shingo, T. et al. Erythropoietin regulates the in vitro and in vivo production of neuronal progenitors by mammalian forebrain neural stem cells. J. Neurosci. 21(24):9733-9743 (2001).

Wrighton, N. C., et al. Small peptides as potent mimetics of the protein hormone erythropoietin. Science 273(5274):458-464 (1996).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

In recent years, neurodegenerative disease has become an important concern due to the expanding elderly population which is at greatest risk for these disorders. Neurodegenerative diseases include the diseases which have been linked to the degeneration of neural cells in particular locations of the central nervous system (CNS), leading to the inability of these cells to carry out their intended function. These diseases include Alzheimer's Disease, Multiple Sclerosis (MS), Huntington's Disease, Amyotrophic Lateral Sclerosis, and Parkinson's Disease. In addition, probably the largest area of CNS dysfunction (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. Moreover, brain injuries often result in the loss of neural cells, the inappropriate functioning of the affected brain region, and subsequent behavior abnormalities.

Consequently, it is desirable to supply neural cells to the brain to compensate for degenerate or lost neurons/glial cells in order to treat neurodegenerative diseases or conditions. One approach to this end is to transplant neural cells into the brain of the patient. This approach requires a source of large amounts of neural cells, preferably from the same individual or a closely related individual such that host-versus-graft or graft-versus-host rejections can be minimized. As it is not practical to remove a large amount of neurons or glial cells from one person to transplant to another, a method to culture large quantity of neural cells is necessary for the success of this approach.

Another approach is to induce the production of neural cells in situ to compensate for the lost or degenerate cells. This approach requires extensive knowledge about whether it is possible to produce neural cells in brains, particularly adult brains, and how.

The development of techniques for the isolation and in vitro culture of multipotent neural stem cells (for example, see U.S. Pat. Nos. 5,750,376; 5,980,885; 5,851,832) significantly increased the outlook for both approaches. It was discovered that fetal brains can be used to isolate and culture multipotent neural stem cells in vitro. Moreover, in contrast to the long time belief that adult brain cells are not capable of replicating or regenerating brain cells, it was found that neural stem cells may also be isolated from brains of adult mammals. These stem cells, either from fetal or adult brains, are capable of self-replicating. The progeny cells can again proliferate or differentiate into any cell in the neural cell lineage, including neurons, astrocytes and oligodendrocytes. Therefore, these findings not only provide a source of neural cells which can be used in transplantations, but also demonstrate the presence of multipotent neural stem cells in adult brain and the possibility of producing neurons or glial cells from these stem cells in situ.

It is therefore desirable to develop methods of efficiently proliferating neural stem cells for two purposes: to obtain more stem cells and hence neural cells which can be used in transplantation therapies, and to identify methods which can be used to produce more stem cells in situ.

SUMMARY OF THE INVENTION

Figure 1:
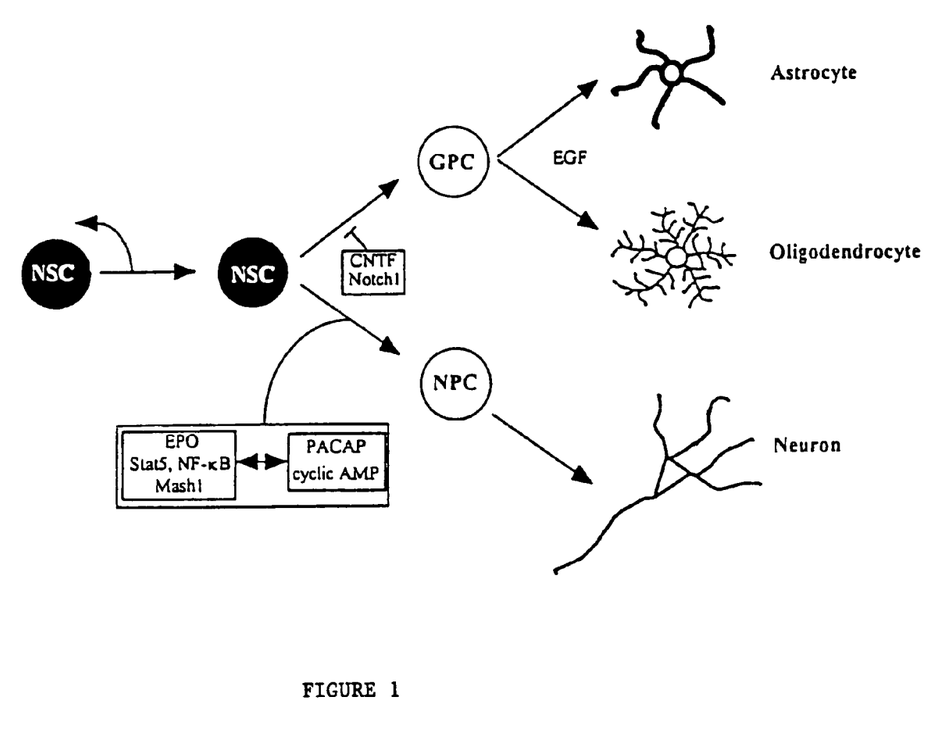
FIG. 1 diagrams a model for neurogenesis and gliogenesis by neural stem cells (NSCs). EGF (or its adult homolog TGFα) induces the self-renewal/expansion of the NSC population. The NSCs will undergo spontaneous differentiation as a default pathway to become glial precursor cells (GPCs). This spontaneous differentiation can be attenuated by CNTF. GPCs differentiate into astrocytes and/or oligodentrocytes, which differentiation is promoted by EGF. Alternatively, NSCs can be instructed by EPO and/or PACAP/cAMP to differentiate to neuronal precursor cells (NPCs), which make neurons only.

This invention relates to a two-step method of producing neural cells in vitro or in vivo. We discovered that neurogenesis and gliogenesis by multipotent neural stem cells (NSCs) involve proliferation and directed differentiation. As shown in FIG. 1, EGF (or its adult homolog TGFα) induces the self-renewal/expansion of the NSC population. The NSCs will undergo-spontaneous differentiation in a default pathway to become glial precursor cells (GPCs). This spontaneous differentiation can be attenuated by ciliary neurotrophic factor (CNTF). GPCs will differentiate into the glial cells, which differentiation is promoted by EGF. Alternatively, NSCs can be instructed by EPO and/or PACAP/cAMP to differentiate to neuronal precursor cells (NPCs), which make neurons only.

Therefore, a two-step process can be used to produce neurons or glial cells: (1) increasing the number of NSCs; and (2) promoting differentiation of the NSCs to either neurons or glial cells by subjecting the NSCs to appropriate conditions which selectively promotes production of neurons or glial cells.

Accordingly, one aspect of the present invention provides a method for producing neuronal precursor cells or glial precursor cells, comprising:
 (a) providing at least one neural stem cell;
 (b) contacting the neural stem cell with a factor selected from the group consisting of prolactin, growth hormone, estrogen, ciliary neurotrophic factor (CNTF), pituitary adenylate cyclase activating polypeptide (PACAP), fibroblast growth factor (FGF), transforming growth factor alpha (TGFα) and epidermal growth factor (EGF) in an amount sufficient to increase the number of neural stem cells; and
 (c) contacting the neural stem cells from step (b) to a factor selected from the group consisting of erythropoietin (EPO), PACAP, prolactin, serotonin, bone morphogenetic protein (BMP) and cAMP in an amount sufficient to enhance the production of neuronal precursor cells or glial precursor cells from the neural stem cells;
 with the proviso that when the factor in step (b) is EGF or FGF, the factor in step (c) is PACAP or prolactin.

Thus, step (b) is performed to increase the number of neural stem cells, which can be achieved by at least one of the following:
 (i) increasing proliferation of the neural stem cell, such as by providing EGF;
 (ii) inhibiting spontaneous differentiation of the neural stem cell, such as by providing CNTF; or
 (iii) promoting survival of the neural stem cell, such as by providing an estrogen.

These two steps, increasing NSCs numbers and enhancing neuron or glia production, may be performed sequentially or concurrently. It is preferable that step (b) is performed prior to step (c).

The factors can be provided by any method established in the art. For example, they can be administered intravascularly, intrathecally, intravenously, intramuscularly, subcutaneously, intraperitoneally, topically, orally, rectally, vaginally, nasally, by inhalation or into the brain. The administration is preferably performed systemically, particularly by subcutaneous administration. The factors can also be provided by administering to the mammal an effective amount of an agent that can increase the amount of endogenous factors in the mammal. For example, the level of prolactin in an animal can be increased by using prolactin releasing peptide.

When the factors are not directly delivered into the brain, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as $NH_2$-arginine-proline-hydroxyproxyproline-glycine-thienylalanine-serine-proline-4-Me-tyrosineψ($CH_2NH$)-arginine-COOH). Alternatively, the factors can be conjugated to the transferrin receptor antibodies as described in U.S. Pat. Nos. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

Although mammals of all ages can be subjected to this method, it is preferable that the mammal is not an embryo. More preferably, the mammal is an adult.

The mammal may suffer from or be suspected of having a neurodegenerative disease or condition. The disease or condition may be a brain injury, such as stroke or an injury caused by a brain surgery. The disease or condition may be aging, which is associated with a significant reduction in the number of neural stem cells. The disease or condition can also be a neurodegenerative disease, particularly Alzheimer's disease, multiple sclerosis, Huntington's disease, amyotrophic lateral sclerosis, or Parkinson's disease.

Alternatively, the neural stem cell may be in a culture in vitro. The cell may be from an animal of any age. Preferably, the animal is not an embryo, and most preferably the animal is an adult.

Another aspect of the present invention provides a method of treating or ameliorating a neurodegenerative disease or medical condition, comprising (a) administering to a mammal a factor which is capable of increasing the number of neural stem cells; and (b) subjecting the mammal to a condition which enhances the production of a lineage restricted cell; whereby production of the lineage restricted cell is enhanced. For example, neurons can be produced to compensate for lost or malfunctioning neurons by administering EGF and EPO. Other factors which are capable of increasing the number of NSCs, such as CNTF, FGF, prolactin, growth hormone, IGF-1, PACAP or estrogen, can also be used instead of EGF or in addition to EGF. Likewise, other factors which can enhance neuron production, such as PACAP or factors which increases cAMP level, can be used in the place of EPO or in addition to EPO.

To produce glial cells to compensate for lost or malfunctioning glial cells, EGF can be administered, which stimulates NSC proliferation, and the resulting NSC will differentiate to glial cells by default. Optionally, inhibitors of the neuronal pathway, such as antibodies of EPO and cAMP signaling inhibitors, can be used to promote glial production. Preferably, a factor that promotes glial formation, such as BMP, is also used to further produce glial cells.

DETAILED DESCRIPTION OF THE INVENTION

This invention relates to a method of selectively producing neural cells, including neurons or glial cells, in vitro or in vivo. Also provided are methods of treating or ameliorating neurodegenerative disease or medical conditions by producing neural cells. Thus, a combination of factors is used to achieve two steps: increasing the number of neural stem cells and instructing the neural stem cells to selectively become neurons or glial cells.

Prior to describing the invention in further detail, the terms used in this application are defined as follows unless otherwise indicated.

Definitions

A "neural stem cell" is a stem cell in the neural cell lineage. A stem cell is a cell which is capable of reproducing itself. In other words, daughter cells which result from stem cell divisions include stem cells. The neural stem cells are capable of ultimately differentiating into all the cell types in the neural cell lineage, including neurons, astrocytes and oligodendrocytes (astrocytes and oligodendrocytes are collectively called glia or glial cells). Thus, the neural stem cells referred to herein are multipotent neural stem cells.

A "neurosphere" is a group of cells derived from a single neural stem cell as the result of clonal expansion. A "primary neurosphere" refers to the neurospheres generated by plating as primary cultures brain tissue which contains neural stem cells. The method for culturing neural stem cells to form neurospheres has been described in, for example, U.S. Pat. No. 5,750,376. A "secondary neurosphere" refers to the neurospheres generated by dissociating primary neurospheres and allowing the individual dissociated cells to form neurospheres again.

A "neural cell" is any cell in the neural lineage. Preferably a neural cell is a neuron or glial cell.

A polypeptide which shares "substantial sequence similarity" with a native factor is at least about 30% identical with the native factor at the amino acid level. The polypeptide is preferably at least about 40%, more preferably at least about 60%, yet more preferably at least about 70%, and most preferably at least about 80% identical with the native factor at the amino acid level.

The phrase "percent identity" or "% identity" of an analog or variant with a native factor refers to the percentage of amino acid sequence in the native factor which are also found in the analog or variant when the two sequences are aligned. Percent identity can be determined by any methods or algorithms established in the art, such as LALIGN or BLAST.

A polypeptide possesses a "biological activity" of a native factor if it is capable of binding to the receptor for the native factor or being recognized by a polyclonal antibody raised against the native factor. Preferably, the polypeptide is capable of specifically binding to the receptor for the native factor in a receptor binding assay.

A "functional agonist" of a native factor is a compound that binds to and activates the receptor of the native factor, although it does not necessarily share a substantial sequence similarity with the native factor.

A "prolactin" is a polypeptide which (1) shares substantial sequence similarity with a native mammalian prolactin, preferably the native human prolactin, a 199-amino acid polypeptide synthesized mainly in the pituitary gland; and (2) possesses a biological activity of the native mammalian prolactin. Thus, the term "prolactin" encompasses prolactin analogs which are the deletional, insertional, or substitutional mutants of the native prolactin. Furthermore, the term "prolactin" encompasses the prolactins from other species and the naturally occurring variants thereof.

In addition, a "prolactin" may also be a functional agonist of a native mammalian prolactin receptor. For example, the functional agonist may be an activating amino acid sequence disclosed in U.S. Pat. No. 6,333,031 for the prolactin receptor; a metal complexed receptor ligand with agonist activities for the prolactin receptor (U.S. Pat. No. 6,413,952); G120RhGH, which is an analog of human growth hormone but acts as a prolactin agonist (Mode et al., 1996); or a ligand for the prolactin receptor as described in U.S. Pat. Nos. 5,506,107 and 5,837,460.

An "EGF" means a native EGF or any EGF analog or variant that shares a substantial amino acid sequence similarity with a native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

In addition, an "EGF" may also be a functional agonist of a native mammalian EGF receptor. For example, the functional agonist may be an activating amino acid sequence disclosed in U.S. Pat. No. 6,333,031 for the EGF receptor, or an antibody that has agonist activities for the EGF receptor (Fernandez-Pol, 1985 and U.S. Pat. No. 5,723,115).

A "PACAP" means a native PACAP or any PACAP analog or variant that shares a substantial amino acid sequence similarity with a native PACAP, as well as at least one biological activity with the native PACAP, such as binding to the PACAP receptor. Useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

In addition, a "PACAP" may also be a functional agonist of a native mammalian PACAP receptor. For example, the functional agonist may be maxadilan, a polypeptide that acts as a specific agonist of the PACAP type-1 receptor (Moro et al., 1997).

An "erythropoietin (EPO)" means a native EPO or any EPO analog or variant that shares a substantial amino acid sequence similarity with a native EPO, as well as at least one biological activity with the native EPO, such as binding to the EPO receptor. Erythropoietin analogs and variants are disclosed, for example, in U.S. Pat. Nos. 6,048,971 and 5,614,184.

In addition, an "EPO" may also be a functional agonist of a native mammalian EPO receptor. For example, the functional agonist may be EMP1 (EPO mimetic peptide 1, Johnson et al., 2000); one of the short peptide mimetics of EPO as described in Wrighton et al., 1996 and U.S. Pat. No. 5,773,569; any small molecular EPO mimetic as disclosed in Kaushansky, 2001; an antibody that activates the EPO receptor as described in U.S. Pat. No. 5,885,574, WO 96/40231, WO 97/48729, Fernandez-Pol, 1985 or U.S. Pat. No. 5,723,115; an activating amino acid sequence as disclosed in U.S. Pat. No. 6,333,031 for the EPO receptor; a metal complexed receptor ligand with agonist activities for the EPO receptor (U.S. Pat. No. 6,413,952), or a ligand for the EPO receptor as described in U.S. Pat. Nos. 5,506,107 and 5,837,460.

"Enhancing" or "promoting" the formation of a cell type means increasing the number of the cell type. Thus, a factor can be used to enhance neuron formation if the number of neurons in the presence of the factor is larger than the number of neurons absent the factor. The number of neurons in the absence of the factor may be zero or more.

A "neurodegenerative disease or condition" is a disease or medical condition associated with neuron loss or dysfunction. Examples of neurodegenerative diseases or conditions include neurodegenerative diseases, brain injuries or CNS dysfunctions. Neurodegenerative diseases include, for example, Alzheimer's disease, multiple sclerosis (MS), macular degeneration, glaucoma, diabetic retinopathy, peripheral neuropathy, Huntington's disease, amyotrophic lateral sclerosis, and Parkinson's disease. Brain injuries include, for example, stroke (e.g., hemorrhagic stroke, focal ischemic stroke or global ischemic stroke) and traumatic brain injuries (e.g. injuries caused by a brain surgery or physical accidents). CNS dysfunctions include, for example, depression, epilepsy, neurosis and psychosis.

"Treating or ameliorating" means the reduction or complete removal of the symptoms of a disease or medical condition.

A mammal "suspected of having a neurodegenerative disease or condition" is a mammal which is not officially diagnosed with the neurodegenerative disease or condition but shows a symptom of the neurodegenerative disease or condition, is susceptible to the neurodegenerative disease or condition due to family history or genetic predisposition, or has previously had the neurodegenerative disease or condition and is subject to the risk of recurrence.

"Transplanting" a composition into a mammal refers to introducing the composition into the body of the mammal by any method established in the art. The composition being introduced is the "transplant", and the mammal is the "recipient". The transplant and the recipient may be syngeneic, allogeneic or xenogeneic. Preferably, the transplantation is an autologous transplantation.

An "effective amount" is an amount of a therapeutic agent sufficient to achieve the intended purpose. For example, an effective amount of a factor to increase the number of neural stem cells is an amount sufficient, in vivo or in vitro, as the case may be, to result in an increase in neural stem cell number. An effective amount of a composition to treat or ameliorate a neurodegenerative disease or condition is an amount of the composition sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

Methods

Neural stem cells (NSCs), such as the ones found in the adult forebrain, are the likely source of restricted neuronal and glial progenitors, which repopulate structures such as the olfactory bulb and corpus callosum, respectively. The mechanisms by which NSCs give rise to restricted progenitors have been unclear prior to this invention.

We found that EGF-responsive NSCs gradually become restricted to a glial lineage. This process is blocked by CNTF, acting through notch1, to maintain NSCs in a multipotent stage. We also found that erythropoietin (EPO) directs the production of restricted neuronal precursors through a mechanism that utilizes Mash1.

Thus, we infused either CNTF or EPO into the lateral ventricles of adult mice for six days, after which we either removed the entire adult ependyma/subependyma to examine the total number of EGF-responsive NSCs or examined the in vivo production of neuronal precursors. CNTF infusion resulted in a 20-25% increase in the number of NSCs, most likely by preventing NSC differentiation into glial precursors. EPO infusion resulted in a 50% reduction in the number of NSCs and a concomitant doubling in neuronal precursors. Infusion of anti-EPO antibodies resulted in a 20% increase in NSCs. Therefore, EGF-responsive NSCs turn over continuously in vivo, a sub-population of which spontaneously differentiates into restricted glial precursors, while another sub-population is directed to the neuronal restricted linage by EPO.

This mechanism is illustrated in FIG. 1. Thus, EGF (or its adult homolog TGFα) induces the self-renewal/expansion of the NSC population. The NSCs undergo spontaneous differentiation as a default pathway to become glial precursor cells (GPCs), which differentiate into glial cells. This spontaneous differentiation can be attenuated by CNTF. Alternatively, NSCs can be instructed by EPO and/or PACAP/cAMP to differentiate to neuronal precursor cells (NPCs), which make neurons only.

Based on this mechanism, we developed a two-step method to produce neural cells. The first step is to increase the number of neural stem cells, which can be achieved by, for example, proliferating neural stem cells (e.g., by EGF, FGF-1, FGF-2, TGFα, estrogen, prolactin, PACAP, growth hormone, and/or IGF-1), inhibiting spontaneous differentiation of neural stem cells (e.g., by CNTF), and/or promoting survival of neural stem cells (e.g., by estrogen). The second step is to enhance neuronal or glial formation from neural stem cells. For example, erythropoietin, prolactin, serotonin, PACAP and/or cyclic AMP can be used to enhance neuron formation, while bone morphogenetic protein (BMP) can be used to enhance glial formation.

The present method can be used in vivo or in vitro. In vitro, the present invention will result in large quantities of neural cells, which can be used in research or therapeutical purposes. In particular, the neural cells can be used in transplantation treatment for neurodegenerative diseases or conditions. In vivo, the present method can increase the number of neural stem cells in situ, and enhance neuronal or glial formation from the enlarged pool of neural stem cells. The resulting neural cells can migrate to appropriate places in the nervous system to enhance neurological functions, or compensate for lost or dysfunctional neural cells. In addition, the in vivo and in vitro applications can be combined. Thus, neural cells, particularly neural stem cells produced by the present method in vitro, can be transplanted into an animal, and factors of the second step can be provided to the animal to enhance differentiation of neural cells in vivo. Optionally, factors of the first step may be provided to the animal as well to further increase the number of neural stem cells that can be subsequently turned to neurons or glial cells.

One particularly interesting neurodegenerative condition is aging. We have found that the number of neural stem cells in the subventricular zone is significantly reduced in aged mice. Accordingly, it will be of particular interest to ameliorate problems associated with aging by the present invention.

In addition, the neural stem cell in the subventricular zone is the source of olfactory neurons, and olfactory dysfunction is a hallmark of forebrain neurodegenerative diseases, such as Alzheimer's, Parkinson's and Huntington's diseases. Disruption of neuronal migration to the olfactory bulb leads to deficits in olfactory discrimination, and doubling the new olfactory interneuons enhances new odor memory (Rochefort et al., 2002). Therefore, the present invention can be used to enhance olfactory discrimination or olfactory memory, as well as physiological functions that are associated with olfaction and olfactory discrimination, such as mating, offspring recognition and rearing.

Another particularly important application of the present invention is the treatment and/or amelioration of brain injuries, such as stroke (Example 2). A brain injury mimicking a stroke was introduced into the motor cortex of rats, and the injured rats showed abnormal behavioral conducts that correlated with the location of the injury. The rats then received prolactin or growth hormone for 7 days, both of which can increase neural stem cell proliferation. Subsequently, the rats received a vehicle control or erythropoietin for 7 days to enhance neuron formation. The rats were then observed for a period of time for behavioral testing, and sacrificed for anatomical analysis.

The results indicate that both prolactin and growth hormone treatments led to an improvement of motor functions in the injured rats. The addition of erythropoietin further enhanced the effect, particularly when combined with prolactin. The anatomical analysis also shows that the number of migrating neurons and/or neural stem cells was increased by every treatment comprising prolactin or growth hormone. In fact, the combination of prolactin and erythropoietin even resulted in complete or partial filling of the cavities created by the brain injury in a majority of the rats. Therefore, these factors, particular combinations of which, can be used to produce neural cells and restore neurological functions in animals with brain injuries.

An intriguing observation is that prolactin and growth hormone led to the restoration of different behavioral functions. Thus, the rats recovered from asymmetrical forelimb usage in balancing after receiving growth hormone, while prolactin acted to correct abnormal positioning of the forelimb during swimming. Therefore, different factors may lead to different cellular migration patterns or the production of different cells, which participate in different neural functions. Accordingly, it is preferable that multiple factors are combined in the treatment of diseases or conditions that have complicated symptoms. Preferred combinations include:

(a) prolactin and at least one factor that enhances neuronal or glial differentiation, such as EPO, PACAP, cyclic AMP and/or BMP;
(b) EGF and at least one factor that enhances neuronal or glial differentiation, such as prolactin, EPO, PACAP, cyclic AMP and/or BMP, particularly prolactin and/or PACAP;
(c) at least one factor that increases neural stem cell number in conjunction with prolactin;
(d) at least one factor that increases neural stem cell number in conjunction with PACAP;
(e) at least one factor that increases neural stem cell number in conjunction with EPO; and
(f) combinations of the above.

Particularly preferred combinations include EGF and EPO, EGF and prolactin, EGF and PACAP, EGF and growth hormone (and/or IGF-1), EGF and prolactin and growth hormone (and/or IGF-1), EGF and prolactin and PACAP, prolactin and growth hormone (and/or IGF-1), prolactin and growth hormone (and/or IGF-1) and EPO, prolactin and PACAP and growth hormone (and/or IGF-1). Most preferred combinations include EGF and PACAP, EGF and prolactin, and prolactin and PACAP. Preferably, FGF is not used.

Compositions

The present invention provides compositions comprising at least one factor that is capable of increasing neural stem cell numbers and at least one factor that is capable of enhancing differentiation of neural stem cells. It should be noted that some factors are capable of both functions, such prolactin. PACAP, in addition to enhancing neuronal differentiation, also enhances proliferation of neural stem cells in the presence of another mitogen.

The factors that are useful in the present invention include their analogs and variants that share a substantial similarity and at least one biological activity with the native factors. For example, although the major form of prolactin found in the pituitary gland has a molecular weight of 23 kDa, variants of prolactin have been characterized in many mammals, including humans. Prolactin variants can result from alternative splicing of the primary transcript, proteolytic cleavage and other post-translational modifications. A prolactin variant of 137 amino acids has been described in the anterior pituitary, which is likely to be a product of alternative splicing. A variety of proteolytic products of prolactin have been characterized, particularly the 14-, 16- and 22-kDa prolactin variants, all of which appear to be prolactin fragments truncated at the C-terminus. Other post-translational modification reported for prolactin include dimerization, polymerization, phosphorylation, glycosylation, sulfation and deamidation.

The prolactin useful in the present invention includes any prolactin analog, variant or prolactin-related protein which is capable of increasing neural stem cell number. A prolactin analog or variant is a polypeptide which contains at least about 30% of the amino acid sequence of the native human prolactin, and which possesses a biological activity of prolactin. Preferably, the biological activity of prolactin is the ability to bind prolactin receptors. Although several isoforms of the prolactin receptor have been isolated, for example the long, intermediate and short forms in rat, the isoforms share the same extracellular domain which binds prolactin. Therefore, any receptor isoform can be used to assay for prolactin binding activity. Specifically included as prolactins are the naturally occurring prolactin variants, prolactin-related protein, placental lactogens, S179D-human prolactin (Bernichtein et al., 2001), prolactins from various mammalian species, including but not limited to, human, other primates, rat, mouse, sheep, pig, and cattle, and the prolactin mutants described in U.S. Pat. Nos. 6,429,186 and 5,955,346.

Similarly, in addition to native EGF, an EGF analog or variant can also be used, which should share a substantial amino acid sequence similarity with the native EGF, as well as at least one biological activity with the native EGF, such as binding to the EGF receptor. Particularly included as an EGF is the native EGF of any species, TGFα, or recombinant modified EGF. Specific examples include, but are not limited to, the recombinant modified EGF having a deletion of the two C-terminal amino acids and a neutral amino acid substitution at position 51 (particularly EGF51gln51; U.S. Patent Application Publication No. 20020098178A1), the EGF mutein (EGF-$X_{16}$) in which the His residue at position 16 is replaced with a neutral or acidic amino acid (U.S. Pat. No. 6,191,106), the 52-amino acid deletion mutant of EGF which lacks the amino terminal residue of the native EGF (EGF-D), the EGF deletion mutant in which the N-terminal residue as well as the two C-terminal residues (Arg-Leu) are deleted (EGF-B), the EGF-D in which the Met residue at position 21 is oxidized (EGF-C), the EGF-B in which the Met residue at position 21 is oxidized (EGF-A), heparin-binding EGF-like growth factor (HB-EGF), betacellulin, amphiregulin, neuregulin, or a fusion protein comprising any of the above. Other useful EGF analogs or variants are described in U.S. Patent Application Publication No. 20020098178A1, and U.S. Pat. Nos. 6,191,106 and 5,547,935.

As another example, useful PACAP analogs and variants include, without being limited to, the 38 amino acid and the 27 amino acid variants of PACAP (PACAP38 and PACAP27, respectively), and the analogs and variants disclosed in, e.g., U.S. Pat. Nos. 5,128,242; 5,198,542; 5,208,320; 5,326,860; 5,623,050; 5,801,147 and 6,242,563.

Erythropoietin analogs and variants are disclosed, for example, in U.S. Pat. Nos. 6,048,971 and 5,614,184.

Further contemplated in the present invention are functional agonists of prolactin or additional factors useful in the present invention. These functional agonists bind to and activate the receptor of the native factor, although they do not necessarily share a substantial sequence similarity with the native factor. For example, maxadilan is a polypeptide that acts as a specific agonist of the PACAP type-1 receptor (Moro et al., 1997).

Functional agonists of EPO have been extensively studied. EMP1 (EPO mimetic peptide 1) is one of the EPO mimetics described in Johnson et al., 2000. Short peptide mimetics of EPO are described in, e.g., Wrighton et al., 1996 and U.S. Pat. No. 5,773,569. Small molecular EPO mimetics are disclosed in, e.g., Kaushansky, 2001. Antibodies that activate the EPO receptor are described in, e.g., U.S. Pat. No. 5,885,574; WO 96/40231 and WO 97/48729).

Antibodies that have agonist activities for the EGF receptor are described, e.g., in Fernandez-Pol, 1985 and U.S. Pat. No. 5,723,115. In addition, activating amino acid sequences are also disclosed in U.S. Pat. No. 6,333,031 for the EPO receptor, EGF receptor, prolactin receptor and many other cell surface receptors; metal complexed receptor ligands with agonist activities for the prolactin and EPO receptors can be found in U.S. Pat. No. 6,413,952. Other methods of identifying and preparing ligands for receptors, e.g., EPO and prolactin receptors, are described, for example, in U.S. Pat. Nos. 5,506,107 and 5,837,460.

It should be noted that the effective amount of each analog, variant or functional agonist may be different from that for the native factor or compound, and the effective amount in each case can be determined by a person of ordinary skill in the art according to the disclosure herein. Preferably, the native factors, or analogs and variants that share substantial sequence similarity with the native factors, are used in the present invention.

Pharmaceutical compositions are also provided, comprising the factors as described above, and a pharmaceutically acceptable excipient and/or carrier.

The pharmaceutical compositions can be delivered via any route known in the art, such as parenterally, intrathecally, intravascularly, intravenously, intramuscularly, transdermally, intradermally, subcutaneously, intranasally, topically, orally, rectally, vaginally, pulmonarily or intraperitoneally. Preferably, the composition is delivered into the central nervous system by injection or infusion. More preferably it is delivered into a ventricle of the brain, particularly the lateral ventricle. Alternatively, the composition is preferably delivered by systemic routes, such as subcutaneous administration. For example, we have discovered that prolactin, growth hormone, IGF-1, PACAP and EPO can be effectively delivered by subcutaneous administration to modulate the number of neural stem cells in the subventricular zone.

When the composition is not directly delivered into the brain, and factors in the composition do not readily cross the blood brain barrier, a blood brain barrier permeabilizer can be optionally included to facilitate entry into the brain. Blood brain barrier permeabilizers are known in the art and include, by way of example, bradykinin and the bradykinin agonists described in U.S. Pat. Nos. 5,686,416; 5,506,206 and 5,268,164 (such as NH$_2$-arginine-proline-hydroxyproxyproline-glycine-thienylalanine-serine-proline-4-Me-tyrosineψ (CH$_2$NH)-arginine-COOH). Alternatively, the factors can be conjugated to the transferrin receptor antibodies as described in U.S. Pat. No. 6,329,508; 6,015,555; 5,833,988 or 5,527,527. The factors can also be delivered as a fusion protein comprising the factor and a ligand that is reactive with a brain capillary endothelial cell receptor, such as the transferrin receptor (see, e.g., U.S. Pat. No. 5,977,307).

The pharmaceutical compositions can be prepared by mixing the desired therapeutic agents with an appropriate vehicle suitable for the intended route of administration. In making the pharmaceutical compositions of this invention, the therapeutic agents are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial cerebral spinal fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the therapeutic agents after administration to the patient by employing procedures known in the art.

For preparing solid compositions such as tablets, the therapeutic agent is mixed with a pharmaceutical excipient to form a solid preformulation composition containing a homogeneous mixture of a compound of the present invention. When referring to these preformulation compositions as homogeneous, it is meant that the therapeutic agents are dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another formulation employed in the methods of the present invention employs transdermal delivery devices ("patches"). Such transdermal patches may be used to provide continuous or discontinuous infusion of the therapeutic agent of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following abbreviations have the following meanings. Abbreviations not defined have their generally accepted meanings.

EGF=epidermal growth factor
PDGF=platelet derived growth factor
DMSO=dimethylsulfoxide
CNTF=ciliary neurotrophic factor
EPO=erythropoietin
NSC=neural stem cell
GPC=glial precursor cell
NPC=neuronal precursor cell
PACAP=pituitary adenylate cyclase activating polypeptide
cAMP=cyclic AMP

MATERIALS AND METHODS

Neural Stem Cell Culture

The protocols for neural stem cell culture are described in detail in U.S. Pat. No. 5,750,376 or Shingo et al., 2001. Briefly, embryonic neural stem cells were prepared from E14 medial and lateral ganglionic eminences. Adult neural stem cells were prepared from the subventricular zone of adult mice. The tissue was cultured in basal medium containing 20 ng/ml EGF, or other growth factors as indicated in each case, to form neurospheres. The composition of the basal medium is as follows: DMEM/F12 (1:1); glucose (0.6%); glutamine (2 mM); sodium bicarbonate (3 mM); HEPES (5 mM); insulin (25 µg/ml); transferrin (100 µg/ml); progesterone (20 mM); putrescine (60 µM); and selenium chloride (30 nM).

Seven days later, the neurospheres (primary neurospheres) were passaged by mechanical dissociation and reseeded as single cells (passage 1). For secondary neurospheres, the single cells were then cultured for seven days to form secondary neurospheres.

Infusion of Growth Factors

Two-month-old CD-1 mice (Charles-River, Laval, Quebec, Canada) were anesthetized with sodium pentobarbital (120 mg/kg, i.p.) and implanted with an osmotic pump (Alzet 1007D; Alza Corporation, Palo Alto, Calif.). The cannula was located in the right lateral ventricle (antero-posterior +0.2 mm, lateral +0.8 mm to bregma, and dorsoventral −2.5 mm below dura with the skull leveled between lambda and bregma). Human recombinant EPO (1000 I U/ml), rabbit anti-EPO neutralizing antibody (100 µg/ml), rabbit IgG (100 µg/ml), rat recombinant CNTF (33 µg/ml), or human recombinant EGF (33 µg/ml) was dissolved in 0.9% saline containing 1 mg/ml mouse serum albumin (Sigma). Each animal was infused for 6 consecutive days at a flow rate of 0.5 µl/hr, resulting in a delivery of about 25 IU of EPO, 3 µg of antibodies, or 400 ng of CNTF or EGF per day.

Test Animals for the Stroke Study

Adult male Long-Evans rats (250-350 g) were obtained from Charles River Breeding Farms and were adapted to the colony for two weeks prior to any treatment. A week before surgery the rats were given a baseline testing on the behavioral tests.

Focal Ischemic Injury and Infusion

The animals for the stroke study received unilateral devascularization of the sensorimotor cortex. Using Isoflurane anesthesia, the skin was incised and retracted and the overlying fascia were removed from the skull. A skull opening was made at the following coordinates, taking care not to damage the dura: AP +4.0 to −2.0; L 1.5 to 4 (the parasagittal ridge; Kolb et al., 1997). The dura was cut and retracted from the skull opening. A cotton swab soaked in sterile saline was gently rubbed across the exposed pia and the vessels were removed. A hole was then drilled in the contralateral hemisphere to provide an opening for the cannulae attached to the osmotic minipump at AP −0.5; L 1.5. An osmotic minipump was placed under the skin between the shoulder blades and a tube connected under the skin to the cannulae, which was attached to the skull with fast-drying cement. Once hemostasis had been achieved the scalp was sutured closed with 5-O sterile suture. The animals were given a single injection of Banamine (an analgesic) and returned to their home cage. Sham animals received only anesthesia, the bone opening, and the skin was incised and sutured.

Six days later the animals were assessed using the behavioral test. On the following day the animals were re-anesthetized and the minipump was replaced with a second one containing the appropriate solutions. Sham animals were only anesthetized. The animals were retested 7, 14, and 28 days later to yield behavioral measures on weeks 1, 2, 3, 4, and 6.

Forelimb Inhibition Test

This test has been shown to constitute a sensitive measure of functional integrity of regions of anterior neocortex. In normal rats, swimming is accomplished by propulsion from the hind limbs. The forelimbs are normally inhibited from any stroking and are held immobile and together under the animal's neck. Inhibition of the forelimbs was assessed by filming animals while swimming. Animals were introduced into one end of an aquarium (30 w×90 l×43 h cm) filled to a depth of 25 cm with room temperature water (~25° C.) and filmed as they swim to a 9.5 cm square visible platform. This platform projects 2 cm above the surface of the water and is positioned at the opposite end of the aquarium. Scoring of inhibition was done by counting the number of strokes, if any, made by each forelimb in three swims along the length of the aquarium. A swim was deemed scorable only if the animal did not touch the sides of the aquarium during the swimming trial.

Forelimb Asymmetry Test

Forepaw asymmetry of the animals was determined by filming them from below while in an acrylic cylinder 25 cm in diameter, on an acrylic platform. Preference was determined by separately counting the number of times in 5 minutes that an animal reared and placed the left or right forepaw on the surface of the cylinder in a gesture of postural stabilization. This test allows a measure of asymmetry in forelimb use, a measure that shows a reliable bias to using the limb ipsilateral to the injury.

Brain Anatomical Analysis

At the conclusion of week 6 the animals were given an overdose of Euthanol and intracardially perfused with 0.9% saline and 4% paraformaldehyde in picric acid. The brains were cryoprotected and cut on a Vibratome at 40 microns. Five sets of sections were kept every 400 microns. Two sets were stained, one with Cresyl Violet and one with Doublecortin. The remaining sets were saved. The Cresyl Violet staining was performed on the slides whereas the Doublecortin was performed as an immunohistochemical procedure on free-floating sections. The Cresyl Violet staining allows assessment of lesion extent whereas the Doublecortin stains for a microtubule associated protein that is present in migrating neuronal progenitor cells.

EXAMPLE 1

The Effect of CNTF and EPO In Vivo

To determine the effect of CNTF and EPO in vivo, CNTF or EPO was infused into adult mice for six days as described in Materials and Methods. The brain tissue was then harvested and used to grow neural stem cells as an indication of the number of neural stem cells in the brain after infusion. Alternatively, the brain tissue was stained for tyrosine hydroxylase or Mash1 to determine the extent of neurogenesis.

As described in detail in Shimazaki et al., 2001, CNTF infusion led to a significant increase of the number of primary neurospheres that can be obtained from the brain (about 25%). Moreover, coinfusion of EGF and CNTF increased the number of neural stem cells by about 40%. Therefore, CNTF is capable of increasing neural stem cell numbers, particularly in combination with EGF. CNTF does not stimulate proliferation of neural stem cells, however, as CNTF did not increase the number of BrdU positive cells when BrdU was also given to the animals.

Since CNTF does not promote proliferation or survival of neural stem cells, we hypothesized that CNTF inhibits spontaneous differentiation of neural stem cells. By spontaneously differentiating into a lineage-restricted cell, neural stem cell will not be able to self-renew, and the number of neural stem cells will decrease while the number of differentiated cells increase. Therefore, if CNTF inhibits this spontaneous differentiation, a neurosphere produced in the presence of CNTF should be more expandable and multipotent than a neurosphere produced in its absence.

Accordingly, we compared the expandability and multipotency of neurospheres that were produced in EGF alone or EGF plus CNTF. For expandability, pass 1 neurospheres were dissociated and replated at clonal density to generate pass 2 neurospheres, and the number of pass 2 neurospheres that were derived from a single pass 1 sphere was counted. The results show that the pass 1 neurospheres generated in EGF plus CNTF led to significantly more pass 2 spheres, indicating that these pass 1 spheres contained more expandable cells than spheres generated in EGF alone. For multipotency, the percentages of neuron, oligodendrocyte and astrocyte that could be derived from each neurosphere were determined, and the results show that neurospheres produced in EGF alone generated 4 times as many glial cells than those produced in EGF plus CNTF. Therefore, neural stem cells differentiate to glial cells by default, which can be inhibited by CNTF.

EPO, on the other hand, reduced the number of neural stem cells by about 50% and increased neurogenesis. Therefore, even though neural stem cells spontaneously differentiate to the glial lineage, a portion of neural stem cells can be induced to form neuronal progenitor cells by EPO. Furthermore, infusion of anti-EPO antibodies, but not non-specific IgG, led to an increase of neural stem cells, indicating that there is an on-going neurogenesis process in vivo that involves EPO.

EXAMPLE 2

The Effect of Factor Combinations in a Stroke Model

In order to determine the effect of various combinations of factors in animals that suffer a brain injury, focal ischemic injuries were introduced into the brains of rats as a model of stroke. As a result of the brain injury, the animals had lesions in the motor cortex and behaved abnormally in two behavioral tests. One is the forelimb inhibition test, a sensitive measure of functional integrity of regions of the anterior neocortex. Normal rats inhibit the use of forelimbs when they swim, but when one side of the motor cortex was injured in this experiment, the rats failed to inhibit the use of the contralateral forelimb as the motor cortex controls the contralateral side of the body. In the other test, the forelimb asymmetry test, normal rats use both forelimbs equally when they try to balance themselves. The injured animals, however, preferred to use the ipsilateral forelimb, presumably because they could not control their contralateral forelimbs.

The animals then received various test factors, and the effects of these factors on the forelimb inhibition test and brain anatomy were assessed. As controls, a sham control group received a sham brain injury and no test factors, and a vehicle control group received the brain injury as well as infusions of artificial cerebral spinal fluid (CSF). The treatments each test group received are summarized below:

| Group | Brain Injury | First Infusion (days 1-7) | Second Infusion (days 8-14) |
|---|---|---|---|
| 1 | sham | none | none |
| 2 | yes | CSF | CSF |
| 3 | yes | prolactin | CSF |
| 4 | yes | prolactin | erythropoietin (EPO) |
| 5 | yes | growth hormone | CSF |
| 6 | yes | growth hormone | erythropoietin (EPO) |

The schedule and procedure of the brain injury, infusion, behavioral test and anatomical analysis are described in Materials and Methods.

A. The Effect of Prolactin and Prolactin Plus EPO

Before the brain injury, all rats inhibited both forepaws in the forelimb inhibition test, which is expected from normal rats. After the injury, all ischemic groups (Groups 2-6) failed to inhibit the contralateral forepaw, but they continued to inhibit the ipsilateral forepaw. Upon infusion of the test factors, the two prolactin groups (Groups 3 and 4) showed greater forepaw inhibition. In fact, by the end of the last week (4 weeks after completion of the infusions), the prolactin plus EPO group (Group 4) was indistinguishable from the controls. Therefore, prolactin, and particularly the combination of prolactin and EPO, resulted in a recovery from a representative symptom of stroke.

Anatomically, the prolactin group showed a high degree of doublecortin staining in the brain, indicating that prolactin induced extensive neurogenesis. The rats in the prolactin plus EPO group had an expanded subventricular zone, indicating a significant cell increase in this area. In addition, many doublecortin positive cells appeared in the legioned area, white matter and the lateral ventricle. A stream of doublecortin positive cells could be observed between the subventricular zone and the lesioned area. Since doublecortin is a marker of migrating neuronal progenitor cells, these results indicate that neural stem cells gave rise to neuronal progenitor cells upon treatment, and the progenitor cells migrated to the lesioned area. The new growth in the lesioned area was so extensive that the cavities created by the ischemic injury were completely or partially filled up in a majority of the rats in this group. These anatomical results thus strongly support the behavioral study that prolactin, or the combination of prolactin and EPO, can be used to treat brain injuries such as stroke.

B. The Effect of Growth Hormone and Growth Hormone Plus EPO

The results of the forelimb asymmetry test indicate that although the extent of asymmetry decreased at the end of week six in all the test groups, the groups receiving growth hormone (Groups 3 and 4) showed a faster and more extensive recovery in the first four weeks. These results are consistent with those from the anatomical analysis, which show that growth hormone alone (Group 3) resulted in increased doublecortin positive cells, and the combination of growth hormone and EPO (Growth 4) led to migration of doublecortin positive cells around the lateral ventricle.

Accordingly, growth hormone, either alone or in conjunction with EPO, improved a motor neuron-related function in a stroke model as well as neuron formation/migration in the brain, indicating that growth hormone can be used to treat or ameliorate brain injuries.

Thus, prolactin and the combination of prolactin and EPO improved the motor function of injured rats in the forelimb inhibition test but not the forelimb asymmetry test, while growth hormone and its combination with EPO had the reversed effect. These results demonstrate that different factors can stimulate different neural pathways and enhance the recovery of different neuronal circuits, indicating that it is important to combine various factors for a more complete and effective therapeutic result.

We claim:

1. A method for producing neuronal precursor cells or glial precursor cells, comprising:
    (a) providing at least one neural stem cell;
    (b) contacting the neural stem cell with prolactin in an amount sufficient to increase the number of neural stem cells; and
    (c) contacting the neural stem cells from step (b) with at least one additional factor selected from the group consisting of erythropoietin (EPO), pituitary adenylate cyclase activating polypeptide (PACAP), serotonin, bone morphogenetic protein (BMP) and cAMP in an amount sufficient to enhance the formation of neuronal precursor cells or glial precursor cells from the neural stem cells.

2. The method of claim 1, wherein step (b) is performed prior to step (c).

3. The method of claim 1, wherein steps (b) and (c) are performed concurrently.

4. The method of claim 1, wherein the neural stem cells are not embryonic cells.

5. The method of claim 1, wherein the neural stem cells are adult neural stem cells.

6. The method of claim 1, wherein the neural stem cell of step (a) is located in a mammal.

7. The method of claim 6, wherein the neural stem cell of step (a) located in the mammal is a transplanted cell.

8. The method of claim 7, wherein the transplanted neural stem cell was expanded in culture prior to transplantation into the mammal.

9. The method of claim 6, wherein the factor of step (b) and the at least one additional factor of step (c) are administered into a brain ventricle of the mammal.

10. The method of claim 6, wherein the factor of step (a) is administered by subcutaneous administration.

11. The method of claim 6, wherein the mammal is suffering from or suspected of having a neurodegenerative disease or condition.

12. The method of claim 11, wherein the disease or condition is brain injury.

13. The method of claim 12, wherein the brain injury is a stroke.

14. The method of claim 11, wherein the disease or condition is selected from the group consisting of Alzheimer's disease, multiple sclerosis (MS), Huntington's disease, amyotrophic lateral sclerosis, and Parkinson's disease.

15. The method of claim 1, wherein the factor of step (c) is EPO.

16. A method for producing neuronal precursor cells or glial precursor cells, comprising:
   (a) providing at least one neural stem cell;
   (b) contacting the neural stem cell with a factor selected from the group consisting of estrogen, ciliary neurotrophic factor (CNTF), fibroblast growth factor (FGF), transforming growth factor alpha (TGFα) and epidermal growth factor (EGF) in an amount sufficient to increase the number of neural stem cells; and
   (c) contacting the neural stem cells from step (b) with prolactin.

17. The method of claim 16, wherein step (b) is performed prior to step (c).

18. The method of claim 16, wherein steps (b) and (c) are performed concurrently.

19. The method of claim 16, wherein the neural stem cells are not embryonic cells.

20. The method of claim 16, wherein the neural stem cells are adult neural stem cells.

21. The method of claim 16, wherein the neural stem cell of step (a) is located in a mammal.

22. The method of claim 21, wherein the neural stem cell of step (a) located in the mammal is a transplanted cell.

23. The method of claim 22, wherein the transplanted neural stem cell was expanded in culture prior to transplantation into the mammal.

24. The method of claim 21, wherein the factor of step (b) and the at least one additional factor of step (c) are administered into a brain ventricle of the mammal.

25. The method of claim 21, wherein the factor of step (a) is administered by subcutaneous administration.

26. The method of claim 21, wherein the mammal is suffering from or suspected of having a neurodegenerative disease or condition.

27. The method of claim 26, wherein the disease or condition is brain injury.

28. The method of claim 27, wherein the brain injury is a stroke.

29. The method of claim 26, wherein the disease or condition is selected from the group consisting of Alzheimer's disease, multiple sclerosis (MS), Huntington's disease, amyotrophic lateral sclerosis, and Parkinson's disease.

30. The method of claim 16, wherein the factor of step (b) is estrogen.

* * * * *